(12) United States Patent
Brown et al.

(10) Patent No.: US 8,292,967 B2
(45) Date of Patent: Oct. 23, 2012

(54) METHOD AND APPARATUS FOR USE OF POROUS IMPLANTS

(75) Inventors: David R Brown, Warsaw, IN (US); Brian May, Warsaw, IN (US); Jennifer Woodell-May, Warsaw, IN (US); Jacy C Hoeppner, Warsaw, IN (US); Elizabeth Schlueter, Gainesville, FL (US); Mukesh Kumar, Warsaw, IN (US); John R White, Winona Lake, IN (US); Russell Parrott, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1836 days.

(21) Appl. No.: 11/294,692

(22) Filed: Dec. 5, 2005

(65) Prior Publication Data
US 2006/0241776 A1 Oct. 26, 2006

Related U.S. Application Data

(63) Continuation-in-part of application No. 11/111,123, filed on Apr. 21, 2005, now abandoned.

(51) Int. Cl.
*A61F 2/32* (2006.01)
(52) U.S. Cl. .................................... 623/23.19
(58) Field of Classification Search ..... 623/22.11–23.46
See application file for complete search history.

(56) References Cited

U.S. PATENT DOCUMENTS

| | | | |
|---|---|---|---|
| 3,353,259 A | 11/1967 | Kirkpatrick | |
| 3,605,123 A | 9/1971 | Hahn | |
| 3,677,795 A | 7/1972 | Bokros et al. | |
| 3,808,606 A | 5/1974 | Tronzo | |
| 3,840,904 A | 10/1974 | Tronzo | |
| 3,855,638 A | 12/1974 | Pilliar | |
| 3,896,500 A | 7/1975 | Rambert et al. | |
| 3,905,777 A | 9/1975 | Lacroix | |
| 3,906,550 A | 9/1975 | Rostoker et al. | |

(Continued)

FOREIGN PATENT DOCUMENTS

DE 24 04 214 C3 1/1974

(Continued)

OTHER PUBLICATIONS

International Search Report and Written Opinion for PCT/US2008/002372 mailed Dec. 9, 2008 claiming benefit of U.S. Appl. No. 11/709,549, which claims benefit of U.S. Appl. No. 11/546,500, which claims benefit of U.S. Appl. No. 11/357,868, which claims benefit of U.S. Appl. No. 11/294,692, which claims benefit of U.S. Appl. No. 11/111,123.

(Continued)

*Primary Examiner* — Eduardo C Robert
*Assistant Examiner* — Ann Schillinger
(74) *Attorney, Agent, or Firm* — Harness, Dickey

(57) ABSTRACT

A prosthesis includes an implant defining an attachment surface thereon. A porous insert is selectively coupled to the implant. The porous insert is adapted to be received at the attachment surface of the implant in a retained position. The porous insert is adapted to facilitate tissue ingrowth. In one embodiment the implant comprises a femoral component. The femoral component comprises an inner condylar portion having a first and second lateral sidewalls, an anterior wall and a posterior wall defining a box. The box defines the attachment surface. In other embodiments, the implant comprises a hip stem and an acetabular shell.

16 Claims, 14 Drawing Sheets

U.S. PATENT DOCUMENTS

| | | |
|---|---|---|
| 3,938,499 A | 2/1976 | Bucalo |
| 3,986,212 A | 10/1976 | Sauer |
| 4,051,559 A | 10/1977 | Pifferi |
| 4,164,794 A | 8/1979 | Spector et al. |
| 4,168,326 A | 9/1979 | Broemer et al. |
| 4,184,213 A | 1/1980 | Heimke |
| 4,187,559 A | 2/1980 | Grell et al. |
| 4,205,400 A | 6/1980 | Shen et al. |
| 4,206,271 A | 6/1980 | Norling et al. |
| 4,217,666 A | 8/1980 | Averill |
| 4,224,698 A | 9/1980 | Hopson |
| 4,234,972 A | 11/1980 | Hench et al. |
| 4,285,070 A | 8/1981 | Averill |
| 4,285,071 A | 8/1981 | Nelson et al. |
| 4,307,472 A | 12/1981 | Morris |
| 4,309,488 A | 1/1982 | Heide et al. |
| 4,330,891 A | 5/1982 | Brånemark et al. |
| 4,345,339 A | 8/1982 | Müller et al. |
| 4,351,069 A | 9/1982 | Ballintyn et al. |
| 4,355,428 A | 10/1982 | Deloison et al. |
| 4,362,681 A | 12/1982 | Spector et al. |
| 4,479,271 A | 10/1984 | Bolesky et al. |
| 4,542,539 A | 9/1985 | Rowe, Jr. et al. |
| 4,550,448 A | 11/1985 | Kenna |
| 4,563,778 A | 1/1986 | Roche et al. |
| 4,566,138 A | 1/1986 | Lewis et al. |
| 4,570,271 A | 2/1986 | Sump |
| 4,612,160 A | 9/1986 | Donlevy et al. |
| 4,636,219 A * | 1/1987 | Pratt et al. ................ 623/23.3 |
| 4,644,942 A | 2/1987 | Sump |
| 4,659,331 A | 4/1987 | Matthews et al. |
| 4,666,450 A | 5/1987 | Kenna |
| 4,685,923 A | 8/1987 | Mathys |
| 4,693,721 A | 9/1987 | Ducheyne |
| 4,715,859 A | 12/1987 | Schelhas et al. |
| 4,715,860 A | 12/1987 | Amstutz et al. |
| 4,743,256 A | 5/1988 | Brantigan |
| 4,743,262 A | 5/1988 | Tronzo |
| 4,756,862 A | 7/1988 | Spector et al. |
| 4,769,041 A | 9/1988 | Morscher |
| 4,778,473 A | 10/1988 | Matthews et al. |
| 4,778,474 A | 10/1988 | Homsy |
| 4,795,469 A | 1/1989 | Oh |
| 4,801,301 A | 1/1989 | Noiles |
| 4,813,959 A | 3/1989 | Cremascoli |
| 4,828,565 A | 5/1989 | Duthoit et al. |
| 4,840,632 A | 6/1989 | Kampner |
| 4,842,606 A * | 6/1989 | Kranz et al. ............... 623/23.28 |
| 4,851,006 A | 7/1989 | Tuke |
| 4,854,496 A | 8/1989 | Bugle |
| 4,863,474 A * | 9/1989 | Brown et al. ............. 623/23.54 |
| 4,863,475 A | 9/1989 | Andersen et al. |
| 4,863,538 A | 9/1989 | Deckard |
| 4,871,368 A | 10/1989 | Wagner |
| 4,883,490 A | 11/1989 | Oh |
| 4,883,491 A | 11/1989 | Mallory et al. |
| 4,892,549 A | 1/1990 | Figgie, III et al. |
| 4,904,265 A | 2/1990 | MacCollum et al. |
| 4,919,675 A | 4/1990 | Dietschi et al. |
| 4,923,473 A | 5/1990 | Griss et al. |
| 4,936,847 A | 6/1990 | Manginelli |
| 4,936,856 A | 6/1990 | Keller et al. |
| 4,936,861 A | 6/1990 | Muller et al. |
| 4,944,759 A | 7/1990 | Mallory et al. |
| 4,950,270 A | 8/1990 | Bowman et al. |
| 4,950,299 A | 8/1990 | Noiles |
| 4,955,919 A | 9/1990 | Pappas et al. |
| 4,957,819 A | 9/1990 | Kawahara et al. |
| 4,963,154 A | 10/1990 | Anapliotis et al. |
| 4,969,907 A | 11/1990 | Koch et al. |
| 4,969,910 A | 11/1990 | Frey et al. |
| 4,976,738 A | 12/1990 | Frey et al. |
| 4,978,355 A | 12/1990 | Frey et al. |
| 4,978,356 A | 12/1990 | Noiles |
| 4,978,358 A | 12/1990 | Bobyn |
| 4,997,445 A | 3/1991 | Hodorek |
| 5,004,476 A | 4/1991 | Cook |
| 5,009,665 A | 4/1991 | Serbousek et al. |
| 5,013,324 A | 5/1991 | Zolman et al. |
| 5,018,285 A | 5/1991 | Zolman et al. |
| 5,019,105 A | 5/1991 | Wiley |
| 5,021,062 A | 6/1991 | Adrey et al. |
| 5,021,063 A | 6/1991 | Tääger |
| 5,024,670 A | 6/1991 | Smith et al. |
| 5,027,998 A | 7/1991 | Bugle |
| 5,030,233 A | 7/1991 | Ducheyne |
| 5,047,182 A | 9/1991 | Sundback et al. |
| 5,080,672 A | 1/1992 | Bellis |
| 5,080,674 A | 1/1992 | Jacobs et al. |
| 5,080,685 A | 1/1992 | Bolesky et al. |
| 5,084,051 A | 1/1992 | Tormala et al. |
| 5,092,897 A | 3/1992 | Forte |
| 5,096,518 A | 3/1992 | Fujikawa et al. |
| 5,098,435 A | 3/1992 | Stednitz et al. |
| 5,104,410 A | 4/1992 | Chowdhary |
| 5,108,432 A * | 4/1992 | Gustavson ................ 623/23.54 |
| 5,126,103 A | 6/1992 | Ishizaki et al. |
| 5,133,764 A | 7/1992 | Pappas et al. |
| 5,152,796 A | 10/1992 | Slamin |
| 5,152,797 A | 10/1992 | Luckman et al. |
| 5,156,626 A | 10/1992 | Broderick et al. |
| 5,163,961 A | 11/1992 | Harwin |
| 5,167,502 A | 12/1992 | Kawahara et al. |
| 5,176,711 A | 1/1993 | Grimes |
| 5,181,928 A | 1/1993 | Bolesky et al. |
| 5,192,329 A | 3/1993 | Christie et al. |
| 5,198,308 A | 3/1993 | Shetty et al. |
| 5,201,766 A | 4/1993 | Georgette |
| 5,203,787 A | 4/1993 | Noblitt et al. |
| 5,211,665 A | 5/1993 | Ku |
| 5,226,915 A | 7/1993 | Bertin |
| 5,236,457 A | 8/1993 | Devanathan |
| 5,236,462 A | 8/1993 | Mikhail |
| 5,246,530 A | 9/1993 | Bugle et al. |
| 5,282,861 A | 2/1994 | Kaplan |
| 5,286,260 A | 2/1994 | Bolesky et al. |
| 5,290,315 A | 3/1994 | DeCarlo, Jr. |
| 5,310,408 A | 5/1994 | Schryver et al. |
| 5,314,490 A | 5/1994 | Wagner et al. |
| 5,323,954 A | 6/1994 | Shetty et al. |
| 5,326,367 A | 7/1994 | Robioneck et al. |
| 5,326,368 A | 7/1994 | Collazo |
| 5,343,877 A | 9/1994 | Park |
| 5,348,788 A | 9/1994 | White |
| 5,358,532 A | 10/1994 | Evans et al. |
| 5,360,448 A | 11/1994 | Thramann |
| 5,360,452 A | 11/1994 | Engelhardt et al. |
| 5,370,692 A | 12/1994 | Fink et al. |
| 5,370,698 A | 12/1994 | Heimke et al. |
| 5,370,702 A | 12/1994 | Jones |
| 5,370,704 A | 12/1994 | DeCarlo, Jr. |
| 5,370,706 A | 12/1994 | Bolesky et al. |
| 5,376,122 A | 12/1994 | Pappas et al. |
| 5,380,325 A | 1/1995 | Lahille et al. |
| 5,397,359 A | 3/1995 | Mittelmeier et al. |
| 5,405,389 A | 4/1995 | Conta et al. |
| 5,415,704 A | 5/1995 | Davidson |
| 5,443,510 A | 8/1995 | Shetty et al. |
| 5,443,512 A | 8/1995 | Parr et al. |
| 5,443,519 A | 8/1995 | Averill et al. |
| 5,484,539 A | 1/1996 | Tersi et al. |
| 5,486,181 A | 1/1996 | Cohen et al. |
| 5,496,372 A | 3/1996 | Hamamoto et al. |
| 5,504,300 A * | 4/1996 | Devanathan et al. .... 219/121.64 |
| 5,505,984 A | 4/1996 | England et al. |
| 5,507,824 A | 4/1996 | Lennox |
| 5,509,933 A | 4/1996 | Davidson et al. |
| 5,534,027 A | 7/1996 | Hodorek |
| 5,535,810 A | 7/1996 | Compton et al. |
| 5,540,713 A | 7/1996 | Schnepp-Pesch et al. |
| 5,545,227 A | 8/1996 | Davidson et al. |
| 5,549,685 A | 8/1996 | Hayes |
| 5,549,691 A | 8/1996 | Harwin |
| 5,549,698 A | 8/1996 | Averill et al. |
| 5,549,701 A | 8/1996 | Mikhail |
| 5,571,187 A | 11/1996 | Devanathan |
| 5,571,194 A | 11/1996 | Gabriel |

| Patent No. | Date | Inventor |
|---|---|---|
| 5,571,198 A | 11/1996 | Drucker et al. |
| 5,571,200 A | 11/1996 | Cohen et al. |
| 5,571,201 A | 11/1996 | Averill et al. |
| 5,573,401 A | 11/1996 | Davidson et al. |
| 5,593,451 A | 1/1997 | Averill et al. |
| 5,609,641 A | 3/1997 | Johnson et al. |
| 5,609,645 A | 3/1997 | Vinciguerra |
| 5,609,646 A | 3/1997 | Field et al. |
| 5,639,280 A | 6/1997 | Warner et al. |
| 5,658,338 A | 8/1997 | Tullos et al. |
| 5,658,347 A | 8/1997 | Sarkisian et al. |
| 5,658,348 A | 8/1997 | Rohr, Jr. |
| 5,665,119 A | 9/1997 | Koller |
| 5,676,700 A | 10/1997 | Black et al. |
| 5,676,704 A | 10/1997 | Ries et al. |
| 5,688,453 A | 11/1997 | England et al. |
| 5,702,473 A | 12/1997 | Albrektsson et al. |
| 5,702,477 A | 12/1997 | Capello et al. |
| 5,702,483 A | 12/1997 | Kwong |
| 5,702,487 A | 12/1997 | Averill et al. |
| 5,723,011 A | 3/1998 | Devanathan et al. |
| 5,723,014 A | 3/1998 | Laurent et al. |
| 5,725,587 A | 3/1998 | Garber |
| 5,728,510 A | 3/1998 | White |
| 5,734,959 A | 3/1998 | Krebs et al. |
| 5,755,743 A | 5/1998 | Volz et al. |
| 5,755,806 A | 5/1998 | Stalcup et al. |
| 5,782,928 A | 7/1998 | Ries et al. |
| 5,782,929 A | 7/1998 | Sederholm |
| 5,798,308 A | 8/1998 | Chatterjee et al. |
| 5,824,107 A | 10/1998 | Tschirren |
| 5,824,108 A | 10/1998 | Huebner |
| 5,863,295 A | 1/1999 | Averill et al. |
| 5,871,548 A | 2/1999 | Sanders et al. |
| 5,879,398 A | 3/1999 | Swarts et al. |
| 5,879,399 A | 3/1999 | Church |
| 5,879,401 A | 3/1999 | Besemer et al. |
| 5,879,404 A | 3/1999 | Bateman et al. |
| 5,879,405 A | 3/1999 | Ries et al. |
| 5,888,205 A | 3/1999 | Pratt et al. |
| 5,904,720 A | 5/1999 | Farrar et al. |
| 5,916,268 A | 6/1999 | Schollner et al. |
| 5,925,077 A | 7/1999 | Williamson et al. |
| 5,926,685 A | 7/1999 | Krebs et al. |
| 5,931,870 A | 8/1999 | Cuckler et al. |
| 5,938,702 A | 8/1999 | Lopez et al. |
| 5,972,032 A | 10/1999 | Lopez et al. |
| 5,976,148 A | 11/1999 | Charpenet et al. |
| 5,981,828 A | 11/1999 | Nelson et al. |
| 5,989,293 A | 11/1999 | Cook et al. |
| 6,008,432 A | 12/1999 | Taylor |
| 6,013,104 A | 1/2000 | Kampner |
| 6,022,509 A | 2/2000 | Matthews et al. |
| 6,042,611 A | 3/2000 | Noiles |
| 6,042,612 A | 3/2000 | Voydeville |
| 6,049,054 A | 4/2000 | Panchison et al. |
| 6,059,833 A | 5/2000 | Doets |
| 6,063,442 A | 5/2000 | Cohen et al. |
| 6,066,176 A | 5/2000 | Oshida |
| 6,087,553 A | 7/2000 | Cohen et al. |
| 6,099,529 A | 8/2000 | Gertzman et al. |
| 6,129,765 A | 10/2000 | Lopez et al. |
| 6,132,469 A | 10/2000 | Schroeder |
| 6,132,674 A | 10/2000 | Compton et al. |
| 6,136,029 A | 10/2000 | Johnson et al. |
| 6,139,574 A | 10/2000 | Vacanti et al. |
| 6,143,036 A | 11/2000 | Comfort |
| 6,143,293 A | 11/2000 | Weiss et al. |
| 6,149,689 A | 11/2000 | Grundei |
| 6,152,962 A | 11/2000 | DeCarlo, Jr. |
| 6,162,257 A | 12/2000 | Gustilo et al. |
| 6,165,222 A | 12/2000 | Hoeppner et al. |
| 6,176,879 B1 | 1/2001 | Reischl et al. |
| 6,187,050 B1 | 2/2001 | Khalili et al. |
| 6,192,272 B1 | 2/2001 | Fiedler |
| 6,193,761 B1 | 2/2001 | Treacy |
| 6,197,065 B1 | 3/2001 | Martin et al. |
| 6,203,844 B1 | 3/2001 | Park |
| 6,206,924 B1 | 3/2001 | Timm |
| 6,217,620 B1 | 4/2001 | Park |
| 6,228,121 B1 | 5/2001 | Khalili |
| 6,231,612 B1 | 5/2001 | Balay et al. |
| 6,240,616 B1 | 6/2001 | Yan |
| 6,253,443 B1 | 7/2001 | Johnson |
| 6,273,891 B1 | 8/2001 | Masini |
| 6,290,726 B1 | 9/2001 | Pope et al. |
| 6,293,971 B1 | 9/2001 | Nelson et al. |
| 6,296,667 B1 | 10/2001 | Johnson et al. |
| 6,302,913 B1 | 10/2001 | Ripamonti et al. |
| 6,306,173 B1 | 10/2001 | Masini |
| 6,309,546 B1 | 10/2001 | Herrmann et al. |
| 6,322,728 B1 | 11/2001 | Brodkin et al. |
| 6,340,370 B1 | 1/2002 | Willert et al. |
| 6,352,559 B1 | 3/2002 | Church |
| 6,365,092 B1 | 4/2002 | Backa et al. |
| 6,376,573 B1 | 4/2002 | White et al. |
| 6,383,224 B1 | 5/2002 | Gie et al. |
| 6,391,251 B1 | 5/2002 | Keicher et al. |
| 6,416,553 B1 | 7/2002 | White et al. |
| 6,432,142 B1 | 8/2002 | Kamiya et al. |
| 6,443,991 B1 | 9/2002 | Running |
| 6,447,543 B1 | 9/2002 | Studer et al. |
| 6,447,550 B1 | 9/2002 | Hunter et al. |
| 6,454,811 B1 | 9/2002 | Sherwood et al. |
| 6,458,161 B1 | 10/2002 | Gibbs et al. |
| 6,461,385 B1 | 10/2002 | Gayer et al. |
| 6,475,243 B1 | 11/2002 | Sheldon et al. |
| 6,497,727 B1 | 12/2002 | Pope et al. |
| 6,506,192 B1 | 1/2003 | Gertzman et al. |
| 6,508,841 B2 | 1/2003 | Martin et al. |
| 6,520,995 B2 | 2/2003 | Church |
| 6,527,774 B2 | 3/2003 | Lieberman |
| 6,527,807 B1 | 3/2003 | O'Neil et al. |
| 6,527,809 B1 | 3/2003 | Doursounian et al. |
| 6,530,958 B1 | 3/2003 | Cima et al. |
| 6,537,321 B1 | 3/2003 | Horber |
| 6,544,472 B1 | 4/2003 | Compton et al. |
| 6,558,428 B2 | 5/2003 | Park |
| 6,572,655 B1 | 6/2003 | Johnson |
| 6,585,772 B2 | 7/2003 | Hunter et al. |
| 6,592,622 B1 | 7/2003 | Ferguson |
| 6,605,293 B1 | 8/2003 | Giordano et al. |
| 6,605,648 B1 | 8/2003 | Johnson et al. |
| 6,610,097 B2 | 8/2003 | Serbousek et al. |
| 6,613,093 B2 | 9/2003 | DeCarlo, Jr. et al. |
| 6,620,200 B1 | 9/2003 | Descamps et al. |
| 6,621,039 B2 | 9/2003 | Wang et al. |
| 6,626,947 B2 | 9/2003 | Lester et al. |
| 6,626,950 B2 | 9/2003 | Brown et al. |
| 6,641,616 B1 | 11/2003 | Grundei |
| 6,645,206 B1 | 11/2003 | Zdeblick et al. |
| 6,652,586 B2 | 11/2003 | Hunter et al. |
| 6,660,040 B2 | 12/2003 | Chan et al. |
| 6,660,224 B2 | 12/2003 | Lefebvre et al. |
| RE38,409 E | 1/2004 | Noiles |
| 6,676,704 B1 | 1/2004 | Pope et al. |
| 6,676,892 B2 | 1/2004 | Das et al. |
| 6,682,566 B2 | 1/2004 | Draenert et al. |
| 6,682,567 B1 | 1/2004 | Schroeder |
| 6,686,437 B2 | 2/2004 | Buchman et al. |
| 6,695,884 B1 | 2/2004 | Townley |
| 6,696,073 B2 | 2/2004 | Boyce et al. |
| 6,709,462 B2 | 3/2004 | Hanssen |
| 6,725,901 B1 | 4/2004 | Kramer et al. |
| 6,726,723 B2 | 4/2004 | Running |
| 6,726,725 B2 | 4/2004 | Hunter et al. |
| 6,758,864 B2 | 7/2004 | Storer et al. |
| 6,770,099 B2 | 8/2004 | Andriacchi et al. |
| 6,783,551 B1 | 8/2004 | Metzger et al. |
| 6,800,094 B2 | 10/2004 | Burkinshaw |
| 6,811,569 B1 | 11/2004 | Afriat et al. |
| 6,827,742 B2 | 12/2004 | Hayes, Jr. et al. |
| 6,840,960 B2 | 1/2005 | Bubb |
| 6,866,685 B2 | 3/2005 | Chan et al. |
| 6,869,447 B2 | 3/2005 | Lee et al. |
| 6,896,703 B2 | 5/2005 | Barbieri et al. |
| 6,908,486 B2 | 6/2005 | Lewallen |
| 6,916,342 B2 | 7/2005 | Frederick et al. |

| | | |
|---|---|---|
| 6,923,833 B2 | 8/2005 | Wasielewski |
| 6,926,740 B2 | 8/2005 | Lewis et al. |
| 6,945,448 B2 | 9/2005 | Medlin et al. |
| 6,981,991 B2 | 1/2006 | Ferree |
| 7,141,073 B2 | 11/2006 | May et al. |
| 7,147,819 B2 | 12/2006 | Bram et al. |
| 7,156,880 B2 | 1/2007 | Evans et al. |
| 7,166,133 B2 | 1/2007 | Evans et al. |
| 7,189,263 B2 | 3/2007 | Erbe et al. |
| 7,192,448 B2 | 3/2007 | Ferree |
| 7,351,371 B2 | 4/2008 | Nelles et al. |
| 2001/0011190 A1 | 8/2001 | Park |
| 2001/0013166 A1 | 8/2001 | Yan |
| 2001/0030035 A1 | 10/2001 | Oda |
| 2002/0016635 A1 | 2/2002 | Despres, III et al. |
| 2002/0040245 A1 | 4/2002 | Lester et al. |
| 2002/0062154 A1 | 5/2002 | Ayers |
| 2002/0068980 A1 | 6/2002 | Serbousek et al. |
| 2002/0071827 A1* | 6/2002 | Petersen et al. ............... 424/93.1 |
| 2002/0123750 A1 | 9/2002 | Eisermann et al. |
| 2002/0139504 A1 | 10/2002 | Klein |
| 2002/0143403 A1 | 10/2002 | Vaidyanathan et al. |
| 2002/0151983 A1 | 10/2002 | Shetty |
| 2002/0197178 A1 | 12/2002 | Yan |
| 2003/0001282 A1 | 1/2003 | Meynen et al. |
| 2003/0013989 A1 | 1/2003 | Obermiller et al. |
| 2003/0033020 A1 | 2/2003 | Hunter et al. |
| 2003/0049299 A1 | 3/2003 | Malaviya et al. |
| 2003/0050703 A1 | 3/2003 | Harris et al. |
| 2003/0050705 A1 | 3/2003 | Cueille et al. |
| 2003/0069639 A1 | 4/2003 | Sander et al. |
| 2003/0083741 A1 | 5/2003 | Woo et al. |
| 2003/0105529 A1 | 6/2003 | Synder |
| 2003/0111752 A1 | 6/2003 | Wood et al. |
| 2003/0114936 A1 | 6/2003 | Sherwood et al. |
| 2003/0135281 A1 | 7/2003 | Hanssen |
| 2003/0144741 A1 | 7/2003 | King et al. |
| 2003/0144742 A1 | 7/2003 | King et al. |
| 2003/0153203 A1 | 8/2003 | Ketelsleger |
| 2003/0153981 A1 | 8/2003 | Wang et al. |
| 2003/0153982 A1 | 8/2003 | Pria |
| 2003/0155686 A1 | 8/2003 | Hawkins et al. |
| 2003/0163202 A1 | 8/2003 | Lakin |
| 2003/0163203 A1 | 8/2003 | Nycz et al. |
| 2003/0171818 A1 | 9/2003 | Lewallen |
| 2003/0200837 A1 | 10/2003 | Matsuura et al. |
| 2003/0220696 A1 | 11/2003 | Levine et al. |
| 2003/0232124 A1 | 12/2003 | Medlin et al. |
| 2003/0236573 A1 | 12/2003 | Evans et al. |
| 2004/0054418 A1 | 3/2004 | McLean et al. |
| 2004/0054421 A1 | 3/2004 | McLean |
| 2004/0064192 A1 | 4/2004 | Bubb |
| 2004/0072010 A1 | 4/2004 | Date et al. |
| 2004/0083004 A1 | 4/2004 | Wasielewski |
| 2004/0088038 A1 | 5/2004 | Dehnad et al. |
| 2004/0098127 A1 | 5/2004 | Charlebois et al. |
| 2004/0102854 A1 | 5/2004 | Zhu |
| 2004/0109853 A1 | 6/2004 | McDaniel |
| 2004/0122521 A1 | 6/2004 | Lee et al. |
| 2004/0126265 A1 | 7/2004 | Takiguchi |
| 2004/0126583 A1 | 7/2004 | Nakamura et al. |
| 2004/0137218 A1 | 7/2004 | Liu et al. |
| 2004/0166340 A1 | 8/2004 | Cairns et al. |
| 2004/0172137 A1 | 9/2004 | Blaylock et al. |
| 2004/0186553 A1 | 9/2004 | Yan |
| 2004/0199258 A1 | 10/2004 | Macara |
| 2004/0199260 A1 | 10/2004 | Pope et al. |
| 2004/0210316 A1 | 10/2004 | King et al. |
| 2004/0225369 A1 | 11/2004 | Lakin et al. |
| 2004/0225371 A1 | 11/2004 | Roger |
| 2004/0229029 A1 | 11/2004 | Bowles et al. |
| 2004/0238410 A1 | 12/2004 | Inoue et al. |
| 2004/0243133 A1 | 12/2004 | Materna |
| 2005/0004677 A1 | 1/2005 | Johnson |
| 2005/0004678 A1 | 1/2005 | Richards |
| 2005/0004680 A1 | 1/2005 | Saladino et al. |
| 2005/0010303 A1 | 1/2005 | Nogier |
| 2005/0025656 A1 | 2/2005 | Bhaduri et al. |
| 2005/0031704 A1 | 2/2005 | Ahn |
| 2005/0032025 A1 | 2/2005 | Bhaduri et al. |
| 2005/0035052 A1 | 2/2005 | Kelly et al. |
| 2005/0048193 A1 | 3/2005 | Li et al. |
| 2005/0049713 A1 | 3/2005 | Garber et al. |
| 2005/0060040 A1 | 3/2005 | Auxepaules et al. |
| 2005/0065307 A1 | 3/2005 | King et al. |
| 2005/0065604 A1 | 3/2005 | Stoll |
| 2005/0071015 A1 | 3/2005 | Sekel |
| 2005/0085820 A1 | 4/2005 | Collins et al. |
| 2005/0085915 A1 | 4/2005 | Steinberg |
| 2005/0087915 A1 | 4/2005 | Pope et al. |
| 2005/0090905 A1 | 4/2005 | Hawkins et al. |
| 2005/0100470 A1 | 5/2005 | Lefebvre et al. |
| 2005/0107883 A1 | 5/2005 | Goodfried et al. |
| 2005/0145364 A1 | 7/2005 | Nakajima |
| 2005/0149199 A1 | 7/2005 | Steinberg |
| 2005/0171614 A1 | 8/2005 | Bacon |
| 2005/0184134 A1 | 8/2005 | Charlebois et al. |
| 2005/0234559 A1 | 10/2005 | Fernandez et al. |
| 2005/0242162 A1 | 11/2005 | Medlin et al. |
| 2005/0246032 A1 | 11/2005 | Bokros et al. |
| 2006/0002810 A1 | 1/2006 | Grohowski |
| 2006/0003179 A1 | 1/2006 | Wang et al. |
| 2006/0018942 A1 | 1/2006 | Rowe et al. |
| 2006/0241781 A1 | 10/2006 | Brown et al. |
| 2007/0021838 A1 | 1/2007 | Dugas et al. |
| 2007/0129809 A1 | 6/2007 | Meridew et al. |
| 2007/0150068 A1 | 6/2007 | Dong et al. |
| 2007/0173948 A1 | 7/2007 | Meridew et al. |
| 2007/0196230 A1 | 8/2007 | Hamman et al. |
| 2007/0243312 A1 | 10/2007 | Bulko |
| 2007/0250175 A1 | 10/2007 | Meridew et al. |
| 2007/0264152 A1 | 11/2007 | Zhao |
| 2008/0147187 A1 | 6/2008 | Bollinger et al. |
| 2009/0084491 A1 | 4/2009 | Uthgenannt et al. |

FOREIGN PATENT DOCUMENTS

| | | |
|---|---|---|
| DE | 3130732 | 5/1983 |
| DE | 3205526 | 9/1983 |
| DE | 8612735 U1 | 3/1989 |
| DE | 41 33 433 | 5/1993 |
| DE | 19726961 | 11/1998 |
| EP | 0 214 885 | 7/1986 |
| EP | 0214885 | 3/1987 |
| EP | 0 378 928 | 7/1990 |
| EP | 0 538 987 | 4/1993 |
| EP | 0551794 | 7/1993 |
| EP | 0577179 | 1/1994 |
| EP | 0612509 | 8/1994 |
| EP | 0648478 | 4/1995 |
| EP | 0 807 426 | 11/1997 |
| EP | 0 985 386 | 3/2000 |
| EP | 1082949 | 3/2001 |
| EP | 1 236 450 | 9/2002 |
| EP | 0 806 921 | 1/2003 |
| EP | 1312323 A2 | 5/2003 |
| EP | 1 384 456 | 1/2004 |
| EP | 1421918 | 5/2004 |
| EP | 1 430 856 | 6/2004 |
| FR | 2 148 322 | 3/1973 |
| FR | 2775586 | 9/1999 |
| FR | 2803740 | 7/2001 |
| GB | 2001247 | 1/1979 |
| WO | WO 92/18069 | 4/1992 |
| WO | WO 96/13233 | 10/1995 |
| WO | WO 96/23459 | 1/1996 |
| WO | WO 00/38598 | 7/2000 |
| WO | WO 02/07652 | 7/2001 |
| WO | WO-01/70141 | 9/2001 |
| WO | WO-2004069107 | 8/2004 |
| WO | WO 2004/080340 | 9/2004 |
| WO | WO-2006007861 | 1/2006 |

OTHER PUBLICATIONS

International Search Report and Written Opinion for PCT/US2007/03811 mailed Sep. 27, 2007.

Michael S. Bradford, M.D. and Wayne G. Paprosky, M.D., F.A.C.S., Total Acetabular Transplant Allograft Reconstruction of the Severely Deficient Acetabulum, Sunrise Hospital and Medical Center, Las Vegas, NV and Rush-Presbyterian-St. Lukes Medical Center, Chicago, IL, 1995 by W.B. Saunders Company, pp. 1-15.

Bram, Martin, et al., High-Porosity Titanium, Stainless Steel, and Superalloy Parts, Advanced Engineering Materials 2000, 2, No. 4, 196-199.

Oliveira, M. V., et al., Porous Structure Characterization in Titanium Coating for Surgical Implants, © 2002, Materials Research, vol. 5, No. 3, 269-273.

Wen, C. E., et al., Novel titanium foam for bone tissue engineering, J. Mater. Res., vol. 17, No. 10, Oct. 2002, 2633-2639.

Wen, C. E., et al., Processing and mechanical properties of autogenous titanium implant materials, Journal of Materials Science: Materials in Medicine 13 (2002), 397-401.

Wen, C. E., Processing of biocompatible porous Ti and Mg, Scripta Materialia 45 (2001) 1147-1153.

Wheeler, K. R., et al., Porous Metals as a Hard Tissue Substitute. Part II. Porous Metal Properties, Biomat., Med. Dev., Art. Org., 1(2), 337-348 (1973).

"Magnum™ large metal articulation, Surgical Technique" brochure, Biomet Orthopedics, Inc., 2004 (12 pages).

International Search Report and Written Opinion for PCT/US2008/002372 mailed Jul. 30, 2008 claiming benefit of U.S. Appl. No. 11/709,549, which claims benefit of U.S. Appl. No. 11/546,500, which claims benefit of U.S. Appl. No. 11/357,868, which claims benefit of U.S. Appl. No. 11/294,692, which claims benefit of U.S. Appl. No. 11/111,123.

Laptev, A. et al. "Study of Production Route for Titanium Parts Combining Very High Porosity and Complex Shape" Powder Metallurgy, vol. 47, No. 1 (2004), pp. 85-92.

* cited by examiner

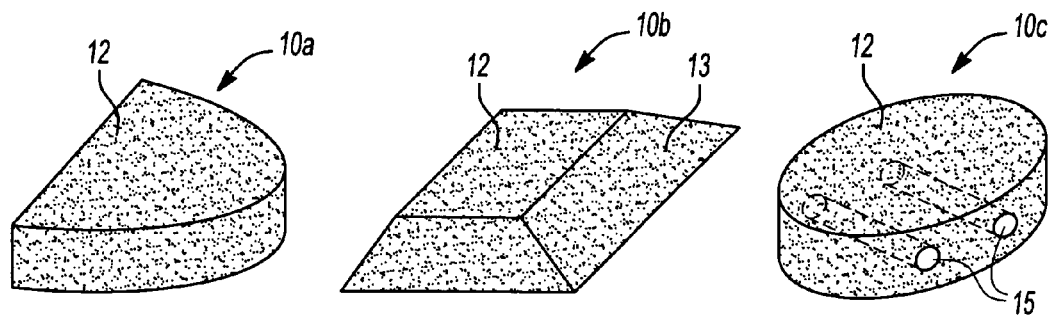
*Fig-1A*  *Fig-1B*  *Fig-1C*
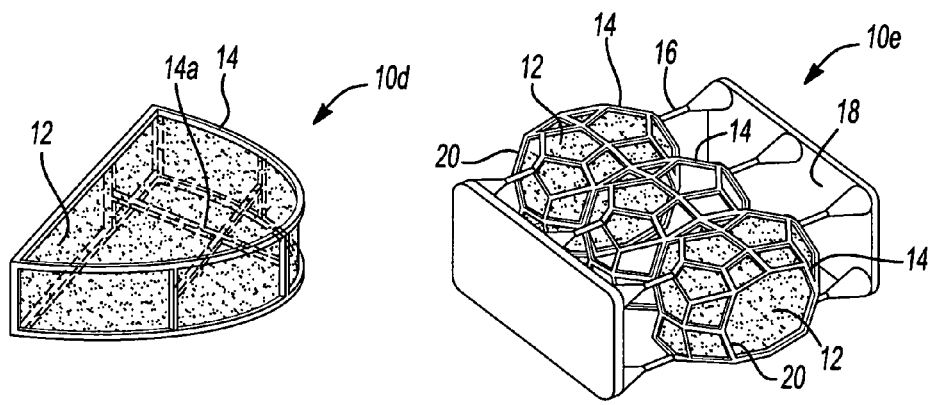
*Fig-1D*  *Fig-1E*

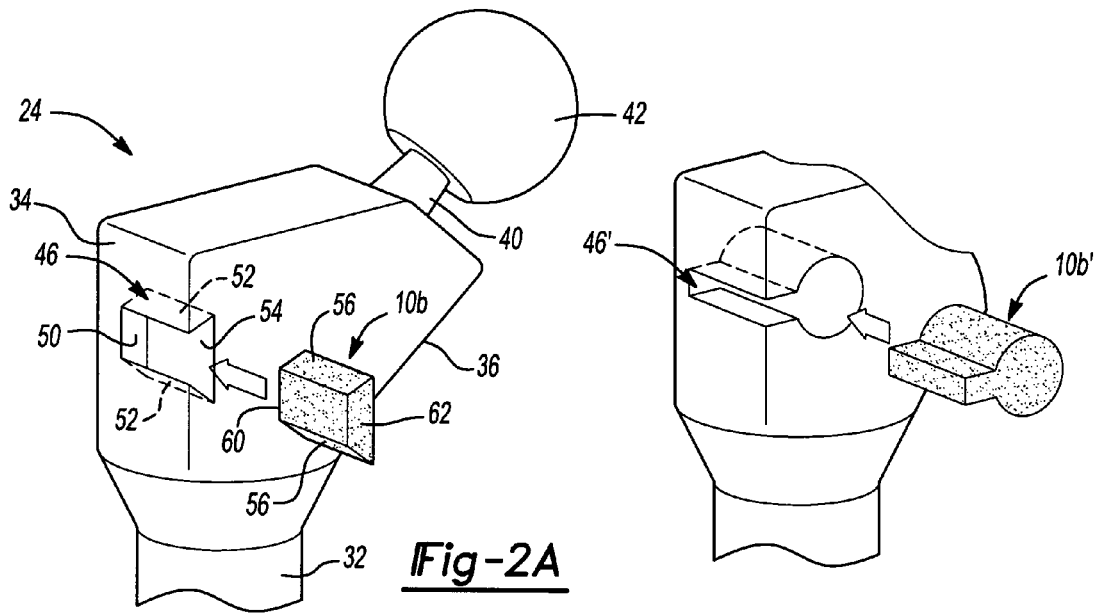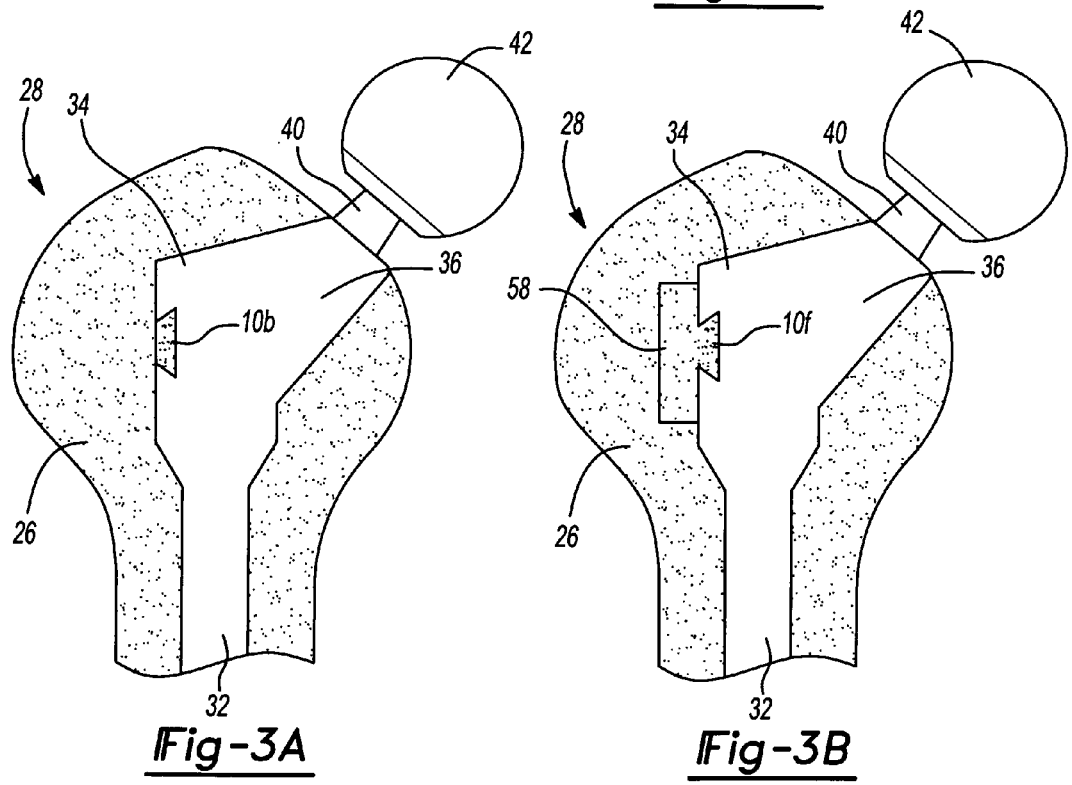

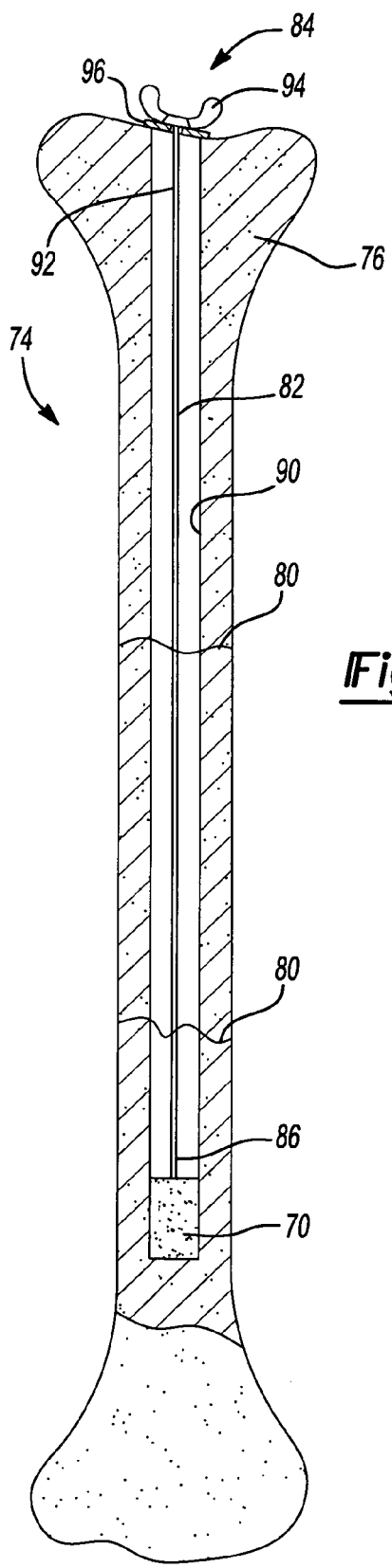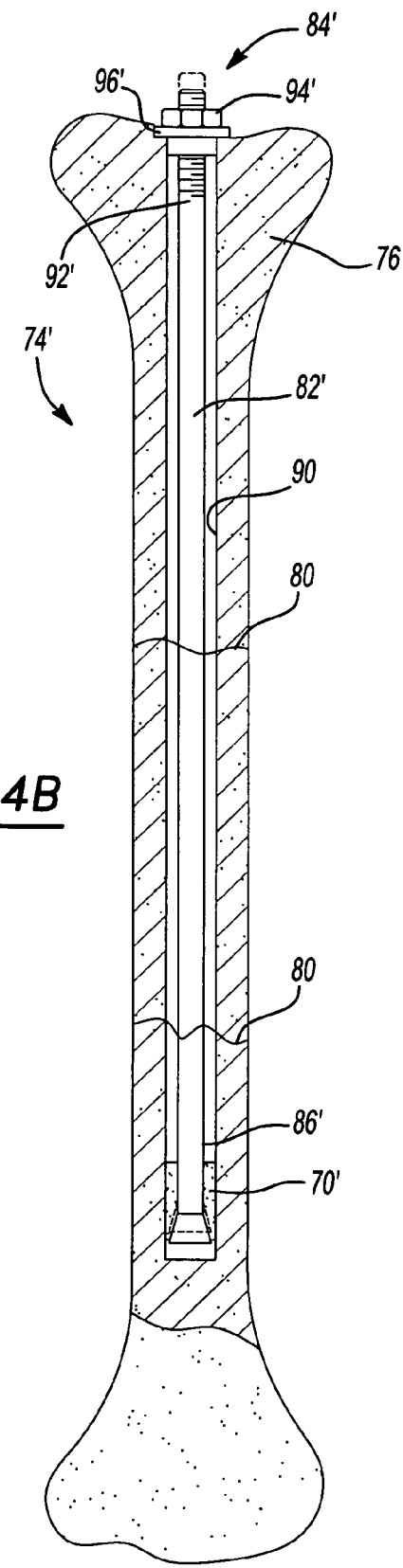

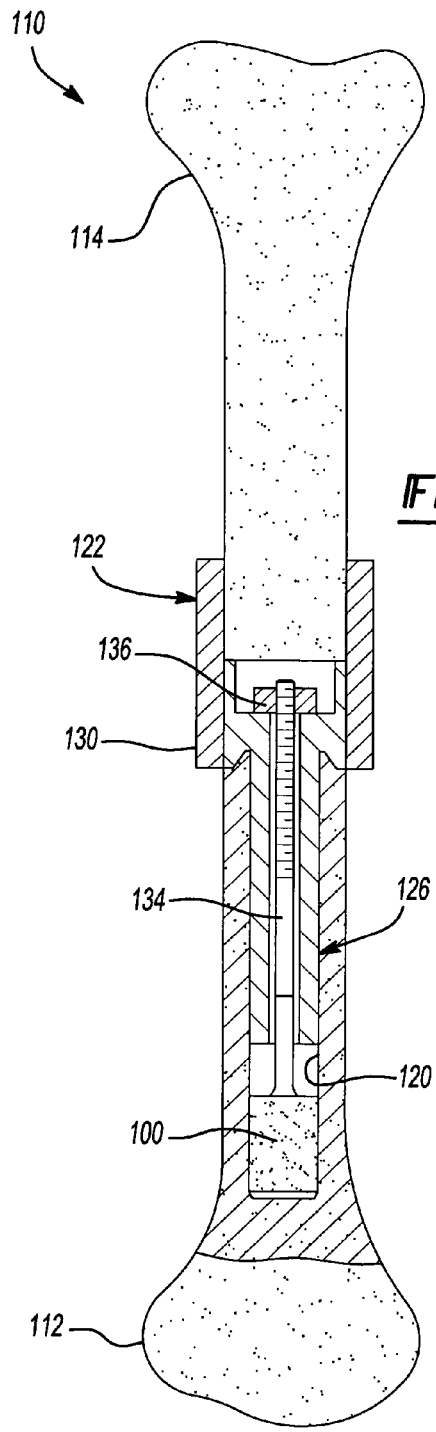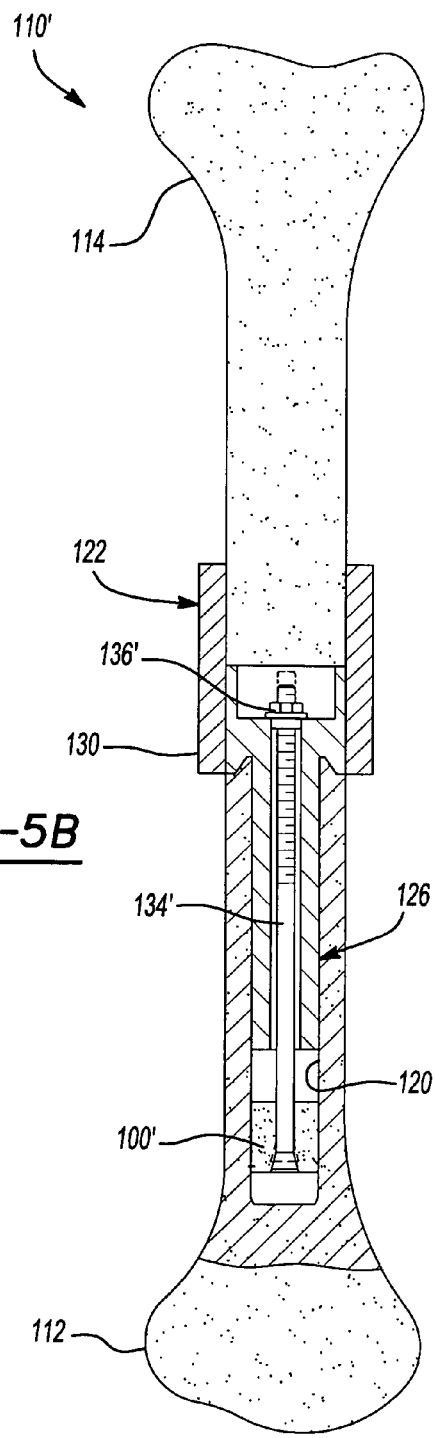

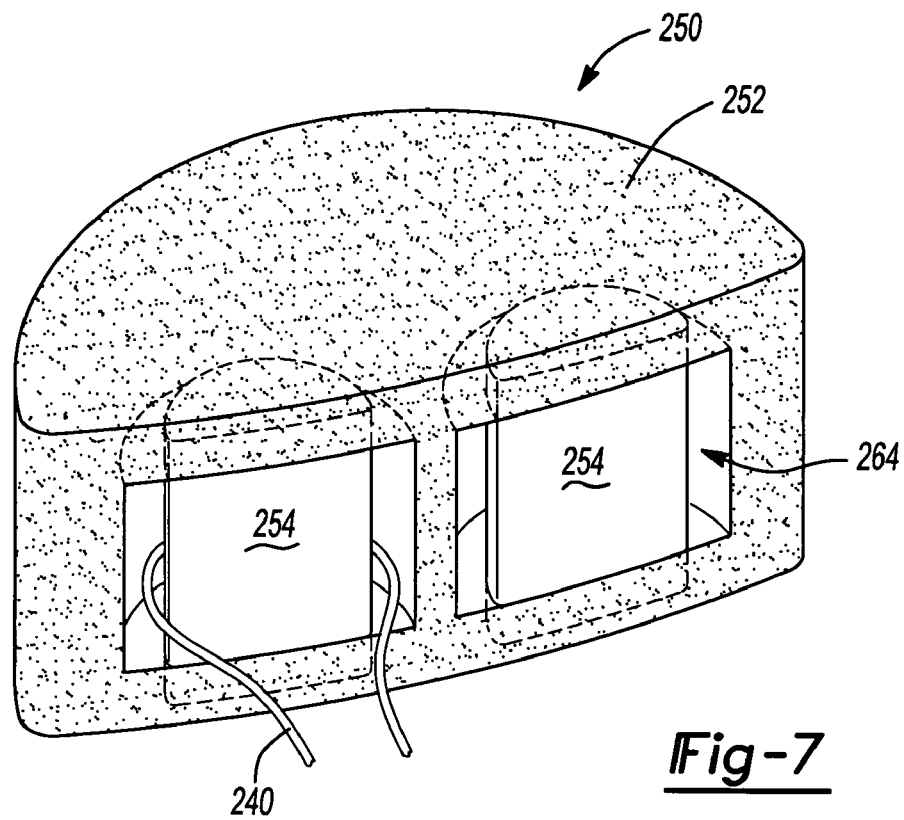
_Fig-7_
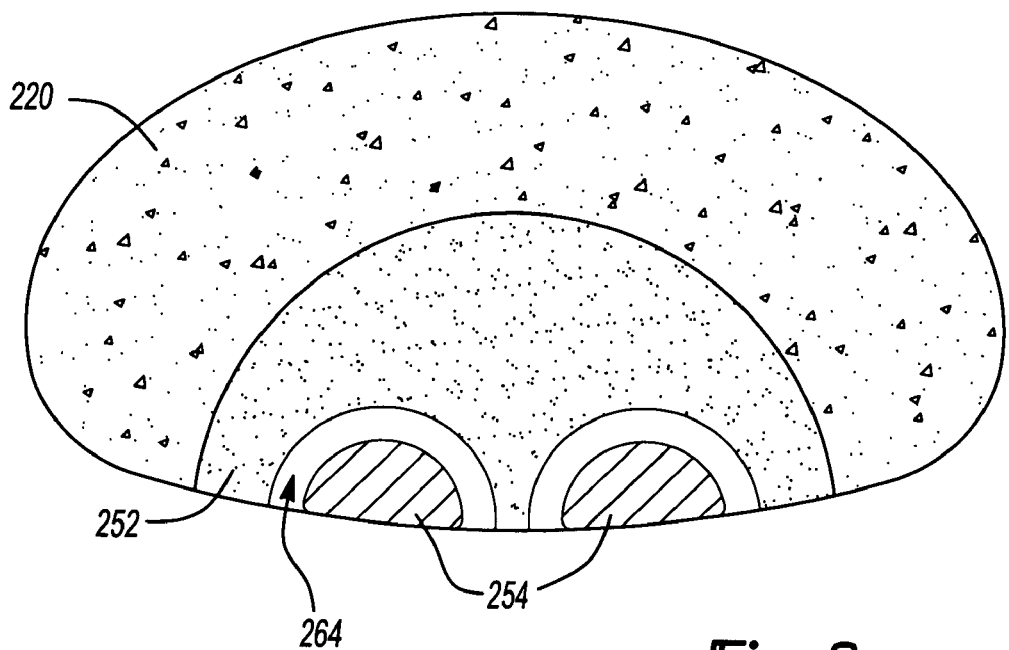
_Fig-8_

US 8,292,967 B2

METHOD AND APPARATUS FOR USE OF POROUS IMPLANTS

CROSS-REFERENCE TO RELATED APPLICATIONS

This application is a continuation-in-part of U.S. patent application Ser. No. 11/111,123 filed on Apr. 21, 2005.

FIELD OF THE INVENTION

The present invention relates to porous implants and more particularly to porous implants for promoting bone growth used in load bearing applications, anchoring or as augments for replacing removed portions of bone.

INTRODUCTION

Porous coated implants have been used to promote biologic fixation of surrounding bony tissue. In one example, porous material may be coated on an exterior surface of a prosthetic implant to encourage ingrowth of surrounding bone into the pore spaces of the porous material. Typically, the porous coating may comprise stainless steel, titanium, titanium alloys, tantalum, cobalt-chromium alloys, ceramics, polymers and other materials that are suited for use in a biocompatible environment. Various joining methods have been employed to attach the porous coating to a desired prosthetic implant. For example, soldering, brazing, adhesive joining, laser welding, diffusion bonding, metallurgic bonds and mechanical joining have been shown to suitably attach the porous material to a desired implant.

SUMMARY OF THE INVENTION

A prosthesis includes an implant defining an attachment surface thereon. A porous insert is selectively coupled to the implant. The porous insert may be adapted to be received at the attachment surface of the implant in a retained position. The porous insert may be adapted to facilitate tissue ingrowth.

In one embodiment the implant comprises a femoral knee component. The femoral knee component comprises an inner condylar portion having a first and second lateral sidewalls, an anterior wall and a posterior wall defining a box. The box defines the attachment surface. In other embodiments, the implant comprises a hip stem and an acetabular shell.

The porous insert may include a framework. The framework may be coated with hydroxyapatite. Biologics such as demineralized bone matrix (DBM), bone morphogenetic proteins (BMP) and antibiotics may be provided as part of the porous insert. According to other features the porous insert may include at least one of an anti-infective agent, osteoconductive agent, autologous blood product, hydrogels, autologous cells, allogenic cells, peptides, bone morphogenetic proteins (BMP), bulk allograft and demineralized bone matrix (DBM).

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1A is a perspective view of an exemplary porous insert according to the present teachings;

FIG. 1B is a perspective view of an exemplary porous insert having an integral retaining surface in the form of tapered outer walls according to the present teachings;

FIG. 1C is a perspective view of an exemplary porous insert having passages incorporated therethrough according to the present teachings;

FIG. 1D is a perspective view of an exemplary porous insert incorporating a metal framework according to the present teachings;

FIG. 1E is a perspective view of a pair of exemplary porous inserts each having a metal framework and shown interconnected through a carrier in a manufacturing step according to the present teachings;

FIG. 2A is a perspective view of a porous insert being implanted into a proximal lateral aspect of a femoral implant;

FIG. 2B is a perspective view of a porous insert being implanted into a proximal lateral aspect of a femoral implant according to additional features;

FIG. 3A is a sectional view of the femoral implant of FIG. 2A shown implanted into a patient;

FIG. 3B is a sectional view of a femoral implant according to additional features shown implanted into a patient;

FIG. 4A is a cutaway view illustrating the environment of a porous anchor used to place a fractured bone in compression;

FIG. 4B is a cutaway view illustrating the environment of a porous anchor according to additional features used to place a fractured bone in compression;

FIG. 5A is a partial cut-away view illustrating the environment of a porous anchor in connection with a device used to secure a bone portion following resection;

FIG. 5B is a partial cut-away view illustrating the environment of a porous anchor according to additional features in connection with a device used to secure a bone portion following resection;

FIG. 7 is a perspective view of a porous implant according to additional features;

FIG. 8 is a sectional view along line 8-8 of FIG. 7;

DETAILED DESCRIPTION OF THE PREFERRED EMBODIMENTS

Figure 6:
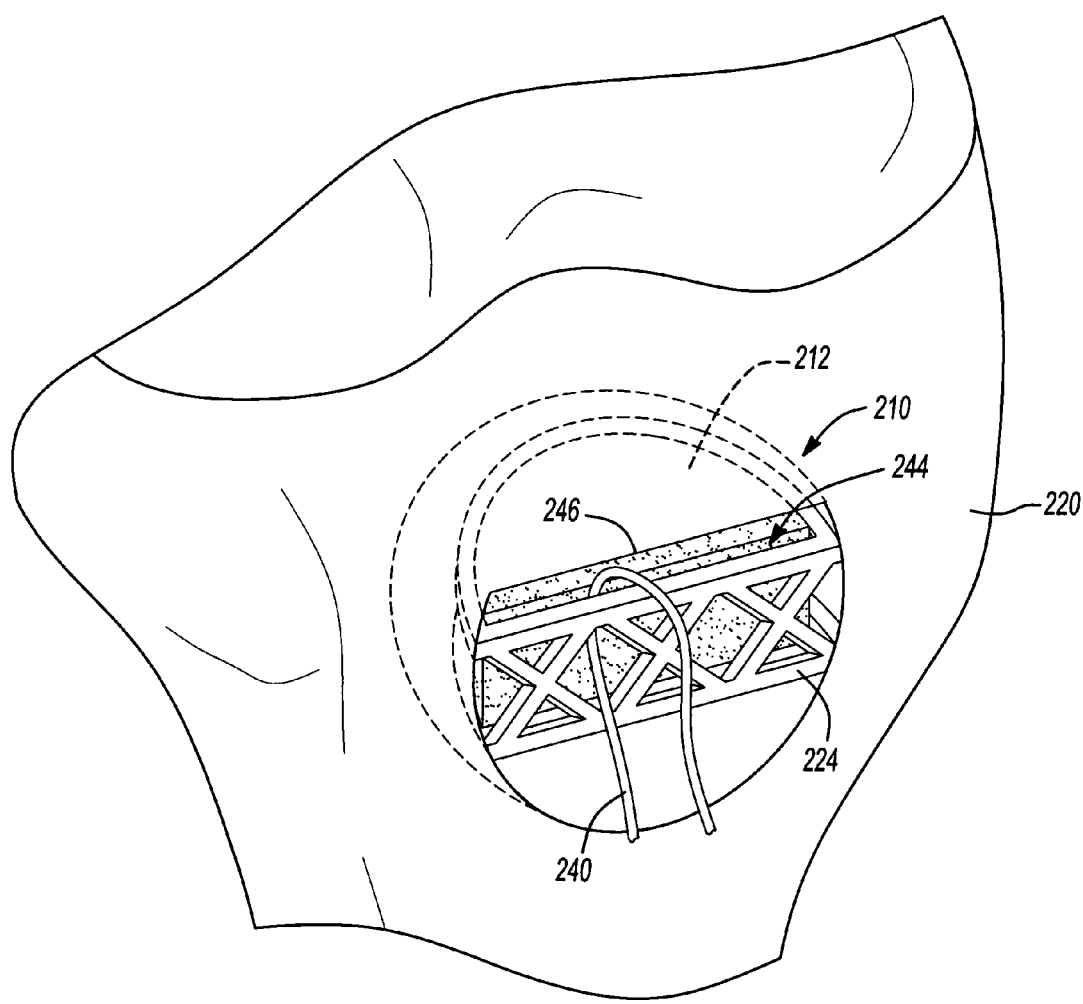
FIG. 6 is a front view of an exemplary porous implant having an attachment structure.

The following description of the embodiment(s) is merely exemplary in nature and is in no way intended to limit the invention, its application, or uses. Moreover, while various shaped metal inserts and certain types of inserts are illustrated, they are merely exemplary in that any shape or any type of implant may include the metal augments.

With initial reference to FIGS. 1A-1E, a series of exemplary porous metal inserts or augments according to the present teachings are shown and identified generally at 10a-10e, respectively. In general, the porous metal augments illustrated in FIGS. 1A-1C comprise a uniform porous metal material or block 12. The porous metal augment 10a has a semi-circular shape. The porous metal augment 10b includes an integral retaining structure in the form of tapered sidewalls 13 adapted to be captured by complementary retaining structure configured on an implant as will be described. The porous metal augment 10c includes apertures 15 formed therethrough. The apertures 15 may be used for attachment purposes for securing the augment 10c at a desired location, or for securing items to the augment 10c.

The porous metal augments illustrated in FIGS. 1D and 1E comprise a uniform porous metal block 12 captured within a solid metal framework 14. As shown in FIG. 1D, a supplemental framework portion 14a may optionally be provided inboard of the framework 14. The framework 14 is adapted to provide additional strength to the augment. The framework 14 may be arranged exclusively on an outboard surface of the porous metal block 12, exclusively within the porous metal block 12 or a combination. The augment 10e illustrated in FIG. 1E shows a series of interconnected frameworks 14, posts 16 and a carrier 18 constructed in a preliminary step. The framework 14 may additionally or alternatively comprise wall surfaces.

FIG. 1C illustrates a porous metal augment having apertures 15 formed therethrough. As will be described in greater detail, the porous metal augments 10a-10e, shown in FIGS. 1A-1E, may be employed in cooperation with an implantable prosthesis and provide a suitable surface area for encouraging ingrowth of natural bone and/or soft tissue. In addition, the porous metal augments 10a-10e may be adapted to provide mechanical strength in a load bearing application, or simply be employed as filler in cooperation with a prosthesis. In this way, the porous metal augments disclosed herein may be load bearing in applications having compression, tension, cantilever, static or dynamic loads. According to other features, the porous metal augments 10a-10e may be used as an anchoring device to facilitate bone fixation or healing in which the bone may be subjected to compression, tension or other loads.

According to the present teachings, the porous metal used in the augments 10a-10e may comprise stainless steel, titanium, titanium alloys, cobalt-chromium alloys and other materials that are suited for use in a biocompatible environment such as disposed on an implantable bone prosthesis. In one method of making the porous metal, a sponge material is utilized as a template. The sponge material may be naturally occurring sponge, such as sponge found in the ocean, or alternatively, an artificial sponge such as a synthetic polymer. The sponge material is then coated or saturated with fine metal particles. Next, the sponge material coated with the fine metal particles is subjected to heat. Exposure to heat causes the sponge to melt away leaving the porous metal block 12. At this point, the porous metal block may be implanted as is, or placed within a solid metal framework (such as framework 14 shown in FIGS. 1D and 1E). It is appreciated that the framework 14 may be arranged around the sponge material prior to melting away of the sponge. Likewise, the sponge material may provide a uniform or non-uniform pattern.

According to another method of making the augments 10a-10e, a laser is utilized to contour a block of suitable material into a desired shape. Again, a suitable material may comprise stainless steel, titanium, titanium alloys, cobalt-chromium alloys and other materials that are suited for use in a biocompatible environment such as disposed on an implantable bone prosthesis. In one implementation, a computer is used to design the desired geometry and properties of the augment. In one method, a bone scan may be performed to create a mathematical model. Another method is by way of computer aided design software. Once the model has been created in the computer, the computer communicates with the laser to melt away portions of material in the block to reproduce the computer model. In one implementation, this process may be used to create the framework 14. A subsequent step requires the porous material 12 to be placed within the framework 14. In another implementation, this process may be used to create the framework 14 and the porous material 12 simultaneously. In such a method, the laser would be utilized to melt identified portions of material to a desired consistency which, when solidified would provide the porous material 12.

In another method of making the augments 10a-10e, sections or layers of material are cut out of sheets of metal and stacked. The stacked layers are subsequently joined by a joining process such as by welding, sintering or diffusion bonding. During a welding operation, the framework and the porous material 12 may be oppositely charged by which a uniform melt may occur between touching surfaces. The material utilized is consistent with those mentioned above. The sheets may be cut by any suitable method such as by laser, machined or other process. It is appreciated that this method may be used to create a framework such as framework 14. A subsequent assembly step may require the porous material 12 to be placed within the framework 14. It is contemplated however that the framework 14 and the porous material 12 may be defined concurrently during the creation of each layer.

With reference now to FIG. 1E, the augment 10e shows a series of interconnected frameworks 14, posts 16 and carrier 18 constructed in a preliminary step. The carrier 18 and posts 16 are used to create a casting. The porous material 12 is then located into the outer frameworks 14 through outer passages 20 defined by the frameworks 14. The intermediate framework 14 (without the porous material 12) along with the carrier 16 and posts 18 are subsequently removed leaving a pair of standalone frameworks 14 having porous material 12 contained therein. Alternatively, the intermediate framework 14 may comprise porous material therein. In another example, the collective series of frameworks 14 may be removed from the carrier 16 and posts 18 and subsequently left as a unitary component rather than being disconnected from each other.

In one exemplary method, the porous material 12 is located within the frameworks 14 as a secondary step. In this implementation, the temperature of the frameworks 14 is raised to a temperature that is below the melting point of the frameworks but enough to cause the frameworks 14 to expand. Additionally or alternatively, the temperature of the porous material 12 is reduced to cause the porous material 12 to contract. Once the desired geometries have been obtained, the porous material 12 is passed through the passages 20 on the frameworks 14. Once the frameworks 14 and the porous material 12 returns to ambient temperature, the porous material 14 has too large of an outer dimension to pass through the passage 20 of the frameworks 14. As a result, the porous material 12 is captured within the frameworks 14.

In another exemplary method, the porous material 12 and the frameworks 14 are initially at ambient temperature. The porous material 12 is then press-fit through the passages 20 of the frameworks 14. Next, the entire assembly 10e is heated to a temperature that causes the contact surfaces of the porous material 12 and frameworks 14 to weld together. Once the assembly 10e returns to ambient temperature, the porous material 12 remains secured to the frameworks 14.

Turning now to FIGS. 2A-3B, a method of utilizing an augment with an implantable bone prosthesis will be described. The exemplary bone prosthesis shown is a femoral hip stem 24. It is appreciated that while the exemplary bone prosthesis is shown as a femoral hip stem 24, other prosthesis may similarly be employed. As illustrated in FIG. 3A natural bone 26 of a femur 28 is shown prepared for the reception of the prosthesis 24. The hip stem 24 generally includes a stem portion 32, a proximal lateral 34, a calcar 36, a neck region 40 and a head 42. Retaining structure 46 is formed on the proximal lateral 34 of the prosthesis 24. It is appreciated that the, retaining structure 46 may be formed at any location on the prosthesis 24 for achieving alternate locations and/or orientations.

The retaining structure 46 generally includes a rear wall 50 and a pair of tapered sidewalls 52 defining a receiving channel 54 therebetween. The receiving channel 54 is adapted to slidably accept augment 10b in a secured relationship. The augment 10b defines complementary sidewalls 56 for slidably nesting between the sidewalls 52 of the receiving channel 54. In one implementation, the geometries of the respective sidewalls 52 and 56 allow for a clearance fit, interference fit or a press fit to ensure the augment 10b is retained by the retaining structure 46 of the prosthesis 24. In this way, no auxiliary fasteners are needed to secure the augment 10b to the prosthesis 24, however, additional fasteners may be used as supplemental attachment if desired. As shown in FIG. 3A the augment 10b is positioned against the natural bone 26 to encourage bone ingrowth thereat to lock the prosthesis 24 into position. In another form, an augment 10f further incorporates an external or outboard portion 58 extending into a portion of the natural bone 26 to fill an area where bone has been removed (FIG. 3B).

It is appreciated that the rear wall 50 may be configured to cooperatively mate with a rear wall 60 of the augment 10b. Similarly, a forward wall 62 may be configured to conform to the outer geometry of the greater trochanter 34. Moreover, it is appreciated that other geometries may be provided for the retaining structure 46 and associated sidewalls 52 to provide a complementary and integral retaining structure for receiving an augment. In the same way, alternate geometrical configurations may be necessary for an augment to cooperatively mate with a given retaining structure on a prosthesis. For example, as illustrated in FIG. 2B, an alternate configuration including an augment 10b' and retaining structure 46' is shown. While the retaining structure 46 is shown integrally formed on a greater trochanter 34 of a hip prosthesis 24, it is appreciated that the retaining structure 46 may be configured elsewhere on the hip prosthesis 24 or on any other implantable prosthesis.

A series of modular augments may be provided having various material properties depending on the nature of the surrounding tissue. In this way, the augments 10a-10e may be tailored to provide a specific porosity or surface finish. In addition, the augments 10a-10e may be made to conform to a specific loading condition experienced in a given prosthesis.

With reference now to FIGS. 4A-5B, another method of utilizing a porous metal augment 10a-10e will be described. As will be described the porous metal augment is utilized as an anchor 70 to aid in bone fixation or healing. It is appreciated that in one form the anchor 70 may be constructed in accordance to the augments 10a-10e described herein. Other anchors employing porous metal construction may also be similarly employed. The following method explained for utilizing the anchor 70 is similar to methods discussed in commonly owned U.S. Pat. Nos. 6,508,841 and 6,197,065 as well as pending U.S. application Ser. No. 10/797,692 which are all expressly incorporated herein by reference.

With initial reference to FIG. 4A, a bone compression device 74 is shown. The bone compression device 74 is utilized to place a bone 76 having at least one fracture 80 in compression to aid in healing. The bone compression device 74 includes the anchor 70, a connecting member 82 and a fastening member 84. Specifically, the anchor 70 is operably connected to a distal end 86 of the connecting member 82. The connecting member 82 extends through a bore 90 formed in the bone 76 and terminates at a proximal end 92. The fastening member 84 includes a nut 94 and washer 96. The nut 94 is threadably engaged to the proximal end 92 of the connecting member 82 and is supported on the washer 96 spanning the diameter of the bore 90. The nut 94 may be translated toward the bone 76 to place the bone 76 under compression to facilitate healing of the fractures 80 in the bone 76. It is appreciated that other arrangements may be provided for securing the proximal end 92 of the connecting member 82 relative the outer surface of the bone 76.

A method of implanting the anchor 70 within the bone 76 will now be described. At the outset, the bore 90 is reamed longitudinally through the bone 76 that transcends the fractures 80. As shown, the exemplary bore 90 may substantially coincide in its longitudinal axis with the natural intramedullary canal of the bone 76. Next, an anchor 70 is selected having an outer diameter suitable to create a press-fit with the inner diameter of the bore 90. A connecting member 82 of appropriate length is chosen and coupled at a distal end 86 to the anchor 70 by any suitable method, such as molded therewith or attached via mechanical or chemical fastening. Next, the anchor 70 is implanted into the bore 90 and advanced to a location beyond the fractures 80, such as a terminal end of the bore 90. Once the intended fixation location is achieved within the bore 90, the washer 96 and nut 94 are connected at the proximal end 92 of the connecting member 82 and advanced toward the bone 76 to achieve a desired tension in the connecting member 82. A suitable tension places the bone 76 under compression and brings respective fractures 80 together to promote healing.

A radial friction force is experienced between the anchor 70 and the surface of the bore 90 while the anchor 70 is in a static position. The friction force is significant enough to hold the anchor 70 in the desired fixation location while the nut 94 is tightened at the proximal end 92 of the connecting member 82 and a resulting tension is created in the connecting member 82. As a result, no supplemental fastening members are required at the anchor 70 and surrounding bone 76 to maintain the anchor 70 in the fixation location.

With reference to FIG. 4B, a bone compression device 74' is shown. The bone compression device 74' incorporates like components as described in relation to the compression device 74 of FIG. 4A. As a result, for simplicity, like components have been designated numerically with a prime suffix. The anchor 70' of FIG. 4B is adapted to urge radially outwardly into the bore 90 of the bone 76 upon tightening of the nut 94'. As illustrated, a first end of the connecting member 82' defines a conical engagement surface for facilitating an outboard force onto the porous anchor 70' as the connecting member 82 is drawn upward (as viewed in FIG. 4B) during tightening of the nut 94'.

Turning now to FIG. 5A, an anchor 100 is shown in use during a segmental bone replacement. Again, in one form the anchor 100 may be constructed in accordance to the augments 10a-10e described herein. Other anchors employing porous metal construction may also be similarly employed. In a segmental bone replacement, it is necessary to resect a mid and/or end portion of a long bone and secure the remaining portion of the bone through an intramedullary device. As shown, a bone assembly 110 includes a first remaining bone portion 112 and a second portion 114, as is the case involving a mid-diaphyseal segment replacement. The second portion 114 may be an orthopedic appliance, or an orthopedic appliance connected to a second remaining bone portion. The second remaining bone portion 114 may be a portion of the same bone as the first remaining bone portion 112, or may be a portion of another bone.

The first remaining bone portion 112 is shown to include a first intramedullary cavity 120, which can be an enlarged longitudinal cylindrically-shaped bore created to a preselected depth from the osteotomy surface. Disposed as part of the bone assembly 110 is a biocompatible bone attachment assembly, shown generally at 122. The bone attachment assembly 122 includes a first bone attachment device 126 which is located about the first remaining bone portion 112. The first bone attachment device 126 may be secured to the second portion 114 through the use of a clamp 130. The bone attachment assembly 122 may also further include a second bone attachment device (not shown) located about the second portion 114, in the situation where the second portion 114 is a second remaining bone portion.

The anchor 100, is utilized to anchor the bone attachment device 126 in an enhanced stationary position within the first intramedullary cavity or bore 120. A connecting rod 134 extends between the anchor 100 and a lock nut 136. The lock nut 136 is threadably received on the connecting rod 134 and may be translated toward the first bone attachment device 126. The anchor 100 may be integrally formed with the connecting rod 134 or coupled thereto as a distinct component. The anchor 100 may also incorporate barbs adapted to resist motion of the anchor once implanted.

As described in relation with the bone compression device 74 illustrated in FIG. 4A, the anchor 100 of FIG. 5A is press fit within the bore 120. As a result, a radial friction force is experienced between the anchor 180 and the surface of the bore 120 while the anchor 100 is in a static position. The friction force is significant enough to hold the anchor 100 in the desired fixation location while the nut 136 is tightened at the proximal end of the connecting member 134 and a resulting tension is created in the connecting member 134. As a result, no supplemental fastening members are required at the anchor 100 and surrounding bone 112 to maintain the anchor 100 in the fixation location.

With reference to FIG. 5B, a bone assembly 110' incorporating an anchor 100' according to additional features is shown in use during a segmental bone replacement. The bone assembly 110' incorporates like components as described in relation to the bone assembly 110 of FIG. 5A. As a result, for simplicity, like components have been designated numerically with a prime suffix. The anchor 100' of FIG. 5B is adapted to urge radially outwardly into the bore 120 of the bone 112 upon tightening of the nut 136'. As illustrated, a first end of the connecting member 134' defines a conical engagement surface for facilitating an outboard force onto the porous anchor 100' as the connecting member 134' is drawn upward (as viewed in FIG. 5B) during tightening of the nut 136'.

Referring now to FIG. 6, an exemplary attachment implant 210 according to the present teachings is illustrated in the environment of a bone member 220, which could be a bone implant or a natural bone, such as, for example, a proximal tibia. It will be appreciated that the attachment implant 210 can be used for reconstructing areas with severe damage or bone loss in various orthopedic salvage procedures, and is not limited for implanting into the proximal tibia or to knee joints.

The implant 210 generally includes a porous material 212 and a framework or support structure 224. The implant 210 may be formed similar to the exemplary augment 10d illustrated in FIG. 1D. As will become appreciated, the support structure 224 of the implant 210 provides attachment points for attaching sutures, grafts, ligaments, tendons or other flexible attachment members 240 by looping the attachment members 240 around a portion of the support structure 224 as illustrated in FIG. 6.

The porous material 212 can be separate or integrally formed with the support structure 224. The porous material can also be a metallic "geostructure", which is a three-dimensional geometric porous engineered structure that is self supporting and is constructed of rigid filaments joined together to form regular, or irregular repeating geometric shapes. The geostructure is described in more detail in U.S. Pat. No. 6,206,924, which is incorporated herein by reference.

The porous material 212, while formed separate or integral with the support structure 224, is offset a distance from the support structure 224 at predetermined locations defining channels 244 to provide access for the attachment members 240. In the exemplary implant 210 the location for attachment is identified at an offset area 244 wherein the support structure 224 is offset from the porous material 212, however, it is appreciated that other areas may be configured in addition to, or alternatively on the implant 210. In one example, body tissue 246 contacts the porous material 212 to facilitate ingrowth.

Turning now to FIGS. 7 and 8, an implant 250 constructed in accordance to additional features is shown. The implant 250 generally comprises porous material 252 and at least one framework or support structure 254. While the exemplary implant 250 illustrates a pair of support structures 254, any number of support structures may be incorporated. The support structures 254 can be elongated members such as solid bars, rods, hollow tubes or other support members. The support structures 254 can be either separate or integral with the porous material 252. The support structures 254 are anchored or otherwise maintained in a secure relationship with the porous material 252 such that flexible attachment members 240 may be looped around influencing a load on the support structures 254. Similar to the offset area 244 of the implant 210, offset areas or channels 264 are defined between the support members 254 and the porous material 252 to allow access for a flexible member 240.

With reference now to FIGS. 9A-15, a method of making a porous implant 310 by selective laser sintering (SLS) will be described. In general, SLS utilizes a high temperature laser to fuse powdered material in successive layers to form a desired shape. The desired shape may correspond to any geometry desired to be implanted such as any of the implants and augments disclosed herein. In one example as illustrated in FIG. 9B, a throughbore 311' may be incorporated on the implant 310' for receiving a fastener or other device during implantation. Typically, a solid model geometry may be constructed through software according to the desired geometry. Once the solid model file is constructed, the data may be communicated to an SLS apparatus for formation of the component. The powdered material may include titanium, cobalt, chromium or combinations thereof. Other powdered materials are contemplated and may be selected according to the desired application.

Figure 9A:
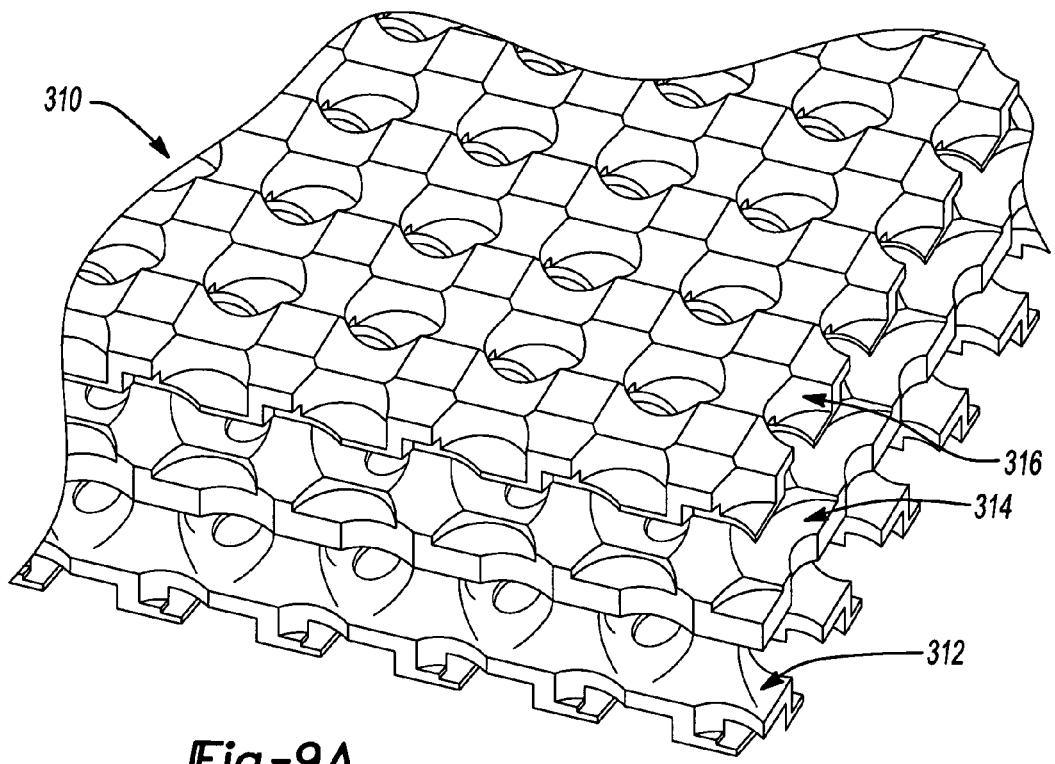
FIG. 9A is a partial perspective view of a porous implant constructed by selective laser sintering.
Figure 9B:
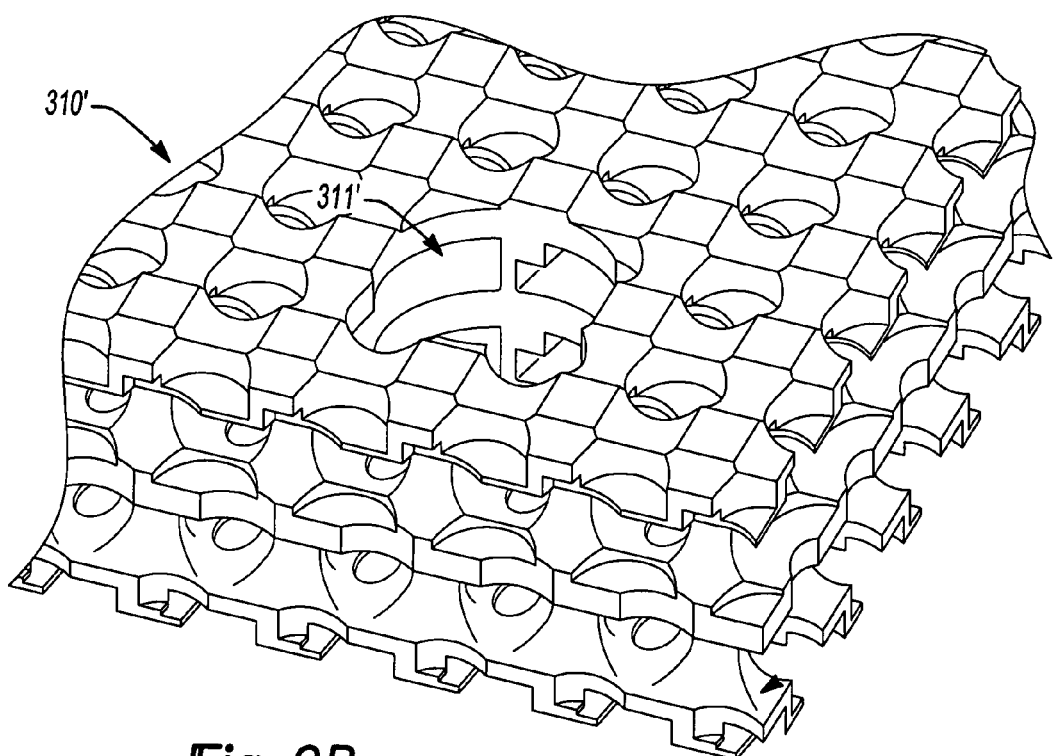
FIG. 9B is a partial perspective view of a porous implant according to additional features and constructed by selective laser sintering.

As illustrated in FIG. 9A, a partial perspective view of the porous implant 310 depicts a first, second and third layer 312, 314 and 316. Formation of the first, second and third layers 312, 314 and 316 are depicted in side view by FIGS. 10-12 and plan view by FIGS. 13-15. It is appreciated that the layers 312-316 are not necessarily formed successively and that other layers may be formed intermediate to the layers 312-316 as depicted in the drawings.

Figure 10:
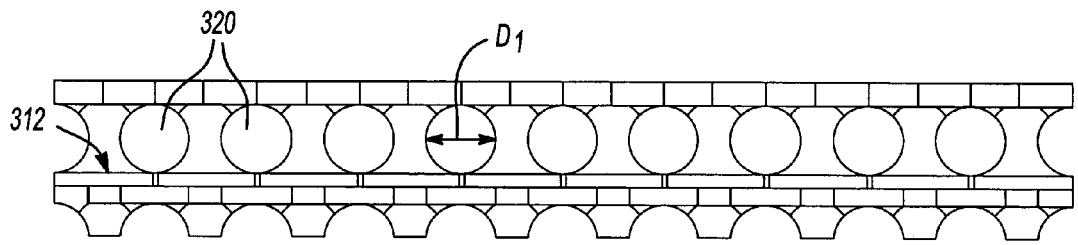
FIGS. 10-12 are sequential side views illustrating layers of the porous implant of FIG. 9 being constructed.
Figure 11:
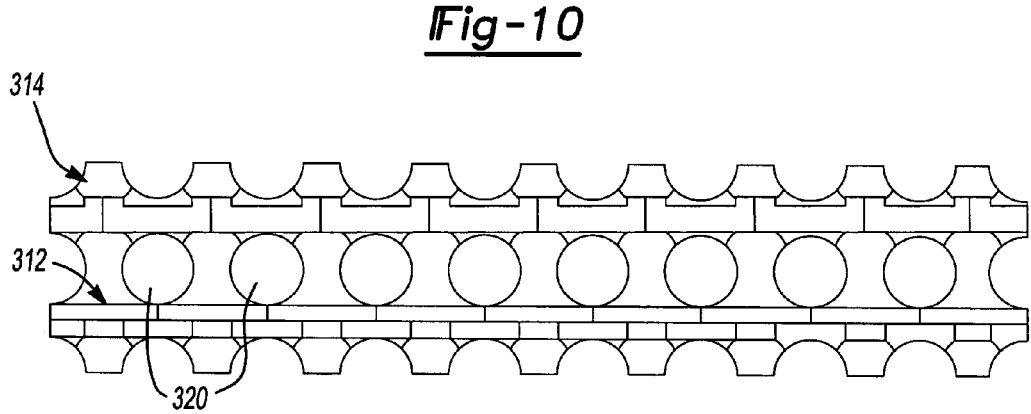
Figure 12:
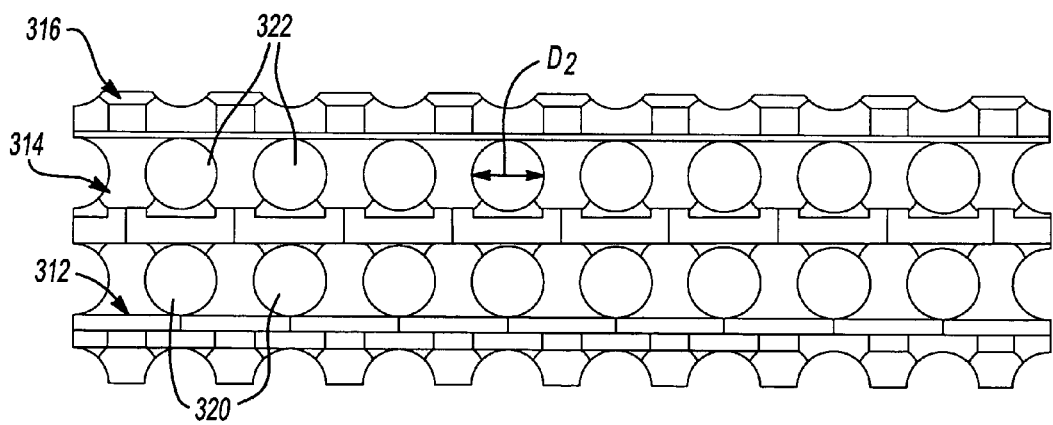

With reference to FIG. 10, the first layer 312 defines a plurality of passages 320. The passages 320 define a diameter $D_1$. The passages are configured to facilitate bone ingrowth. The diameter $D_1$ may be chosen according to the desired application. Referring now to FIGS. 11 and 12, formation of the second and third layers 314 and 316 defines passages 322 having a diameter $D_2$. The diameter $D_2$ may be chosen according to the desired application. It is appreciated that the diameters of the passages 320 and 322 may not necessarily be equivalent. Furthermore, the passages 320 and 322 may define other geometries such as, but not limited to oval, elliptical, triangular, square and rectangular. In addition, while the passages 320 and 322 are shown equally spaced relative to an adjacent passages 320 and 322, the passages may be randomly arranged. Moreover, the passages 320 and 322 may not necessarily be formed on each layer 312, 314 and 316.

Figure 15:
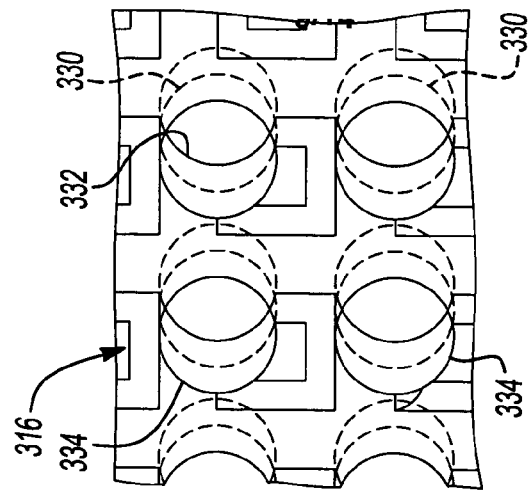
FIGS. 13-15 are sequential top views illustrating layers of the porous implant of FIG. 9 being constructed.
Figure 14:
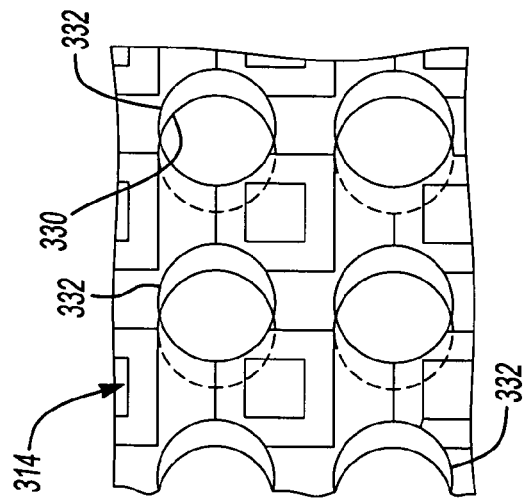
Figure 13:
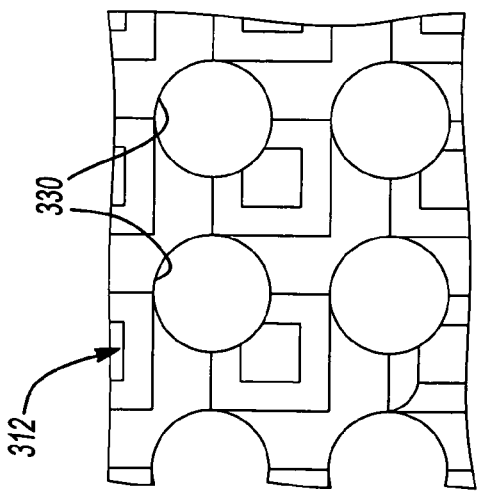

Turning now to FIGS. 13-15, passages 330, 332 and 334 defined on the layers 312-316 in the planar direction are offset relative to each other. More specifically, passages 332 formed on layer 314 (FIG. 14) are axially offset from the passages 330 formed on layer 312 (FIG. 13). The passages 334 formed on layer 316 (FIG. 15) are axially offset from the passages 330 formed on layer 312 and the passages 332 formed on layer 314. Portions of the passages 330, 332 and 334 are aligned in the planar direction and define common passages (FIG. 15).

Constructing the porous implant by SLS allows the respective passages 330-334 to be offset relative to each other in any given direction, allowing a wide range of configurations and porosity. It is appreciated that the passages 320 and 322 defined through a side view of the implant 310 are arranged in an exemplary pattern. More specifically, the passages 320 and 322 may be arranged closer apart, further apart, randomly or any pattern desired. Moreover, the passages 320 and 322, while illustrated as extending completely through the implant 310, may alternatively comprise a plurality of offset passages extending along the plane of each layer 312-316.

Figure 16:
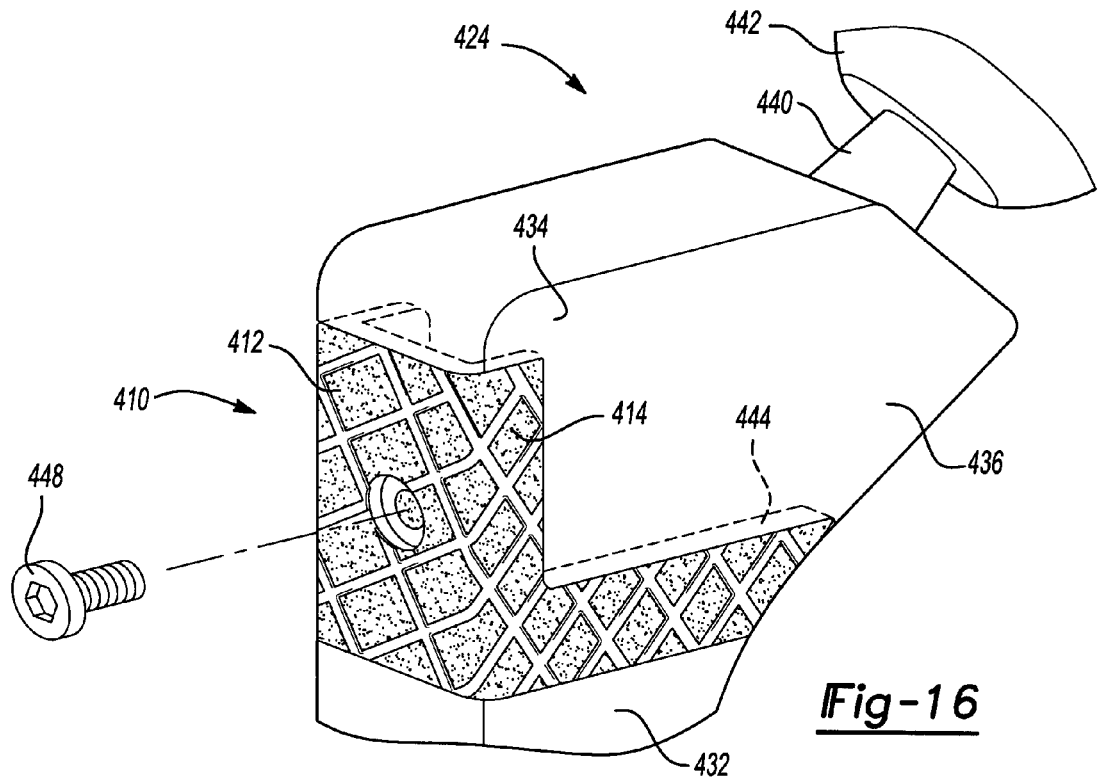
FIG. 16 is a perspective view of a porous insert incorporating a metal framework and adapted to be secured to a proximal lateral aspect of a femoral implant according to the present teachings.

Turning now to FIG. 16, an insert 410 having porous material 412 and a solid metal framework 414 is shown being operably secured to a femoral hip stem 424, or more specifically a proximal lateral aspect of a femoral hip stem. The hip stem 424 generally includes a stem portion 432, a proximal lateral portion 434, a calcar portion 436, a neck region 440 and a head 442. The insert 410 may be constructed by any suitable method, such as those disclosed herein. In one example, the solid metal framework 414 is coated with hydroxyapatite to encourage bone ingrowth. In another example, biologics may be added to the porous material 412 such as demineralized bone matrix (DBM), bone morphogenetic proteins (BMP) and antibiotics. In addition, or alternatively, growth factors such as peptides or others may be added to the porous material.

In one example, the femoral hip stem 424 defines a recess 444 for accepting the insert 410 in a nested position. In one example where boney ingrowth is desired, a surgeon may selectively attach the insert 410 intraoperatively to the femoral hip stem 424. A fastener 448, such as a screw, may be used to secure the insert 410 to the femoral hip stem 424. The framework 414 comprises a structural weight-bearing feature of the insert 410. The cross-hatched representation of the framework 414 is merely exemplary. For example, the framework 414 may comprise other geometries and/or occupy other regions of the insert 410. Moreover, the framework 414 may be exclusively internal to the insert 410 and not necessarily occupy an outer face of the insert 410 as depicted in FIG. 16. In another embodiment, the insert 410 may comprise only porous material 412 and no framework 414. A plurality of inserts may be provided having various configurations and/or porosities such that a surgeon may select an appropriate insert for a given patient.

Figure 17:
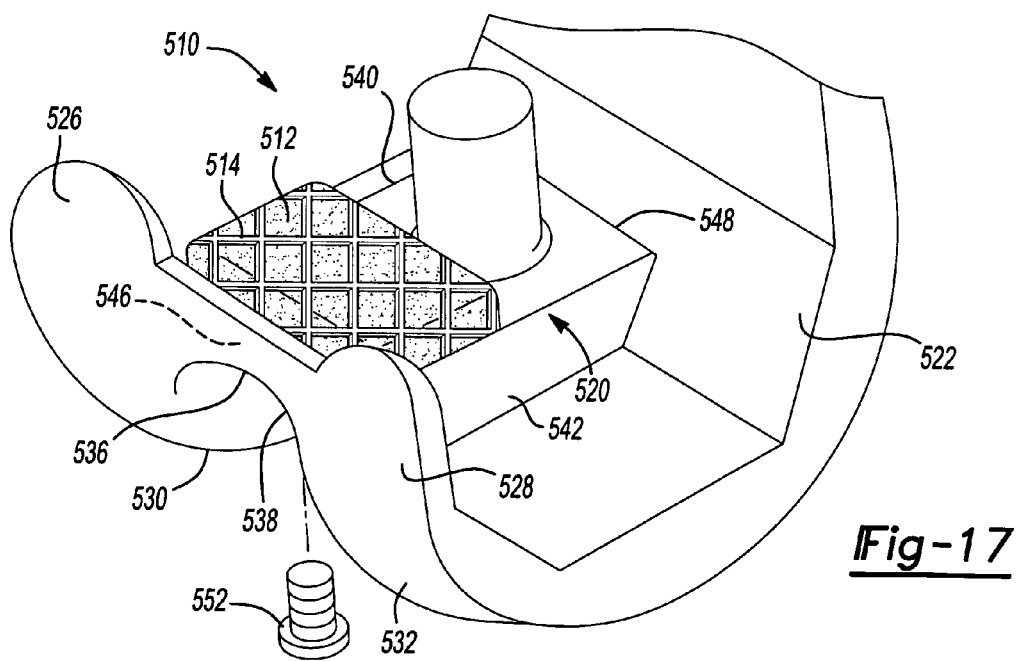
FIG. 17 is a perspective view of a porous insert incorporating a metal framework and adapted to be secured to a femoral box according to the present teachings.

Turning now to FIG. 17, an augment 510 having porous material 512 and a solid metal framework 514 is shown being operably secured to a box 520 of a femoral knee component 522. The femoral knee component 522 generally includes a first condylar portion 526 and a second condylar portion 528 which have a first femoral bearing surface 530 and a second femoral bearing surface 532, respectively. The first and second condylar portions 526, 528 of the femoral knee component 522 are interconnected by an inner condylar portion 536 which defines an inner condylar recess 538. The inner condylar portion 536 includes a first lateral sidewall 540 and a second lateral sidewall 542 which are planar and substantially parallel to each other. The anterior portions of the first and second lateral sidewalls 540, 542 are connected by an anterior wall 546 and the posterior portions of the first and second lateral sidewalls are connected by a posterior wall 548. The inner condylar portion 536 which includes the first and second lateral sidewalls 540, 542 and the anterior and posterior walls 546, 548 define the perimeter of the box 520.

The augment 510 is adapted to be securably positioned atop the box 520. The augment 510 may be intraoperatively attached to an implant for a posterior stabilized knee or a fully constrained knee to replace bone loss. In one example, the augment 510 may be attached to the box 520 by way of a fastener 552 prior to implantation of the femoral knee component 522. In another example, the augment 510 may be attached during implantation of the femoral knee component 522 to fill a gap that may be present between the femoral knee component 522 and a resected femur (not shown). In such an example, it may be necessary to implant the augment from an underside of the femoral knee component (superiorly) through a passage defined through the box 520. In one example, the augment 510 may be attached through a taper fit with the lateral sidewalls 540, 542 and/or the anterior and posterior walls 546 and 548.

The framework 514 comprises a structural weight-bearing feature of the augment 510. The cross-hatched representation of the framework 514 is merely exemplary. For example, the framework 514 may comprise other geometries and/or occupy other regions of the augment 510. Moreover, the framework 514 may be exclusively internal to the augment 510 and not necessarily occupy an outer face of the augment 510 as depicted in FIG. 17. In another embodiment, the augment 510 may comprise only porous material 512 and no framework 514. A plurality of augments may be provided having various configurations and/or porosities such that a surgeon may select an appropriate augment for a given patient.

Figure 18:
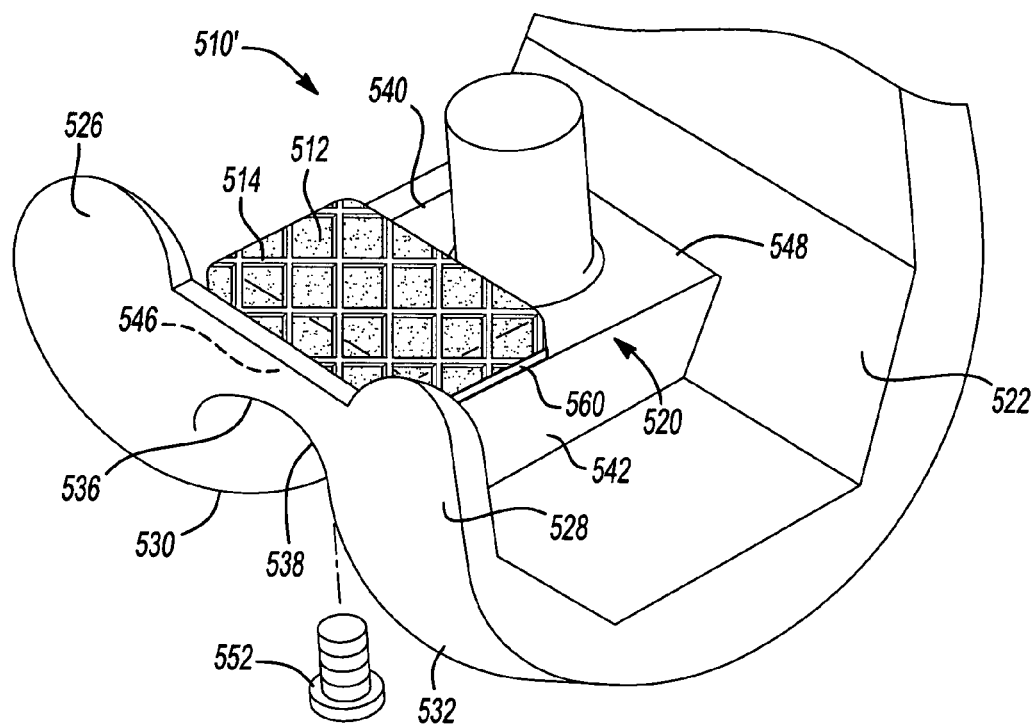
FIG. 18 is a perspective view of a porous insert incorporating a metal framework and adapted to be secured to a femoral box according to the present teachings.

With reference now to FIG. 18, an augment 510' is shown having a solid layer 560 at a lower surface. The solid layer 560 may be located elsewhere through the augment 510' and is operable to provide a barrier or seal. As with insert 410, the augments 510, 510' may be constructed by any suitable method, such as those disclosed herein. In one example, the solid metal framework 514 is coated with hydroxyapatite to encourage bone ingrowth. In another example, biologics may be added to the porous material 512 such as demineralized bone matrix (DBM), bone morphogenetic proteins (BMP) and antibiotics. In addition, or alternatively, growth factors such as peptides or others may be added to the porous material.

Figure 19:
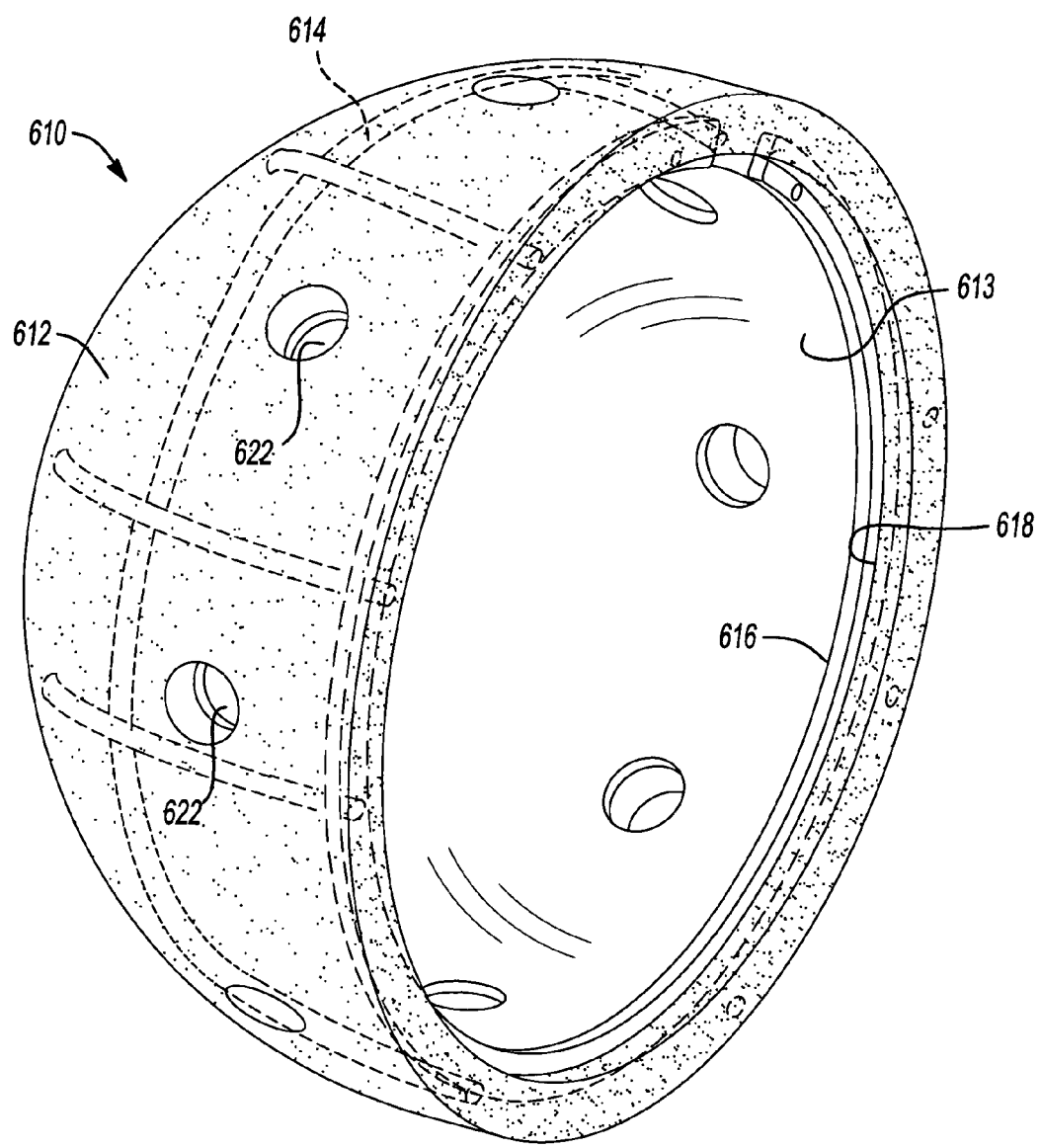
FIG. 19 is a perspective view of porous acetabular cup incorporating a metal framework according to the present teachings.

Turning now to FIG. 19, an acetabular cup 610 having an outer shell including a porous material 612 and an inner shell including non-porous material 613 is shown. The outer shell of the acetabular cup 610 may be constructed by any suitable method, such as sintered laser melting, electron-beam melting or others, such as those disclosed herein. The outer shell may also include a solid metal framework 614. The inner shell may define a bearing insert constructed from any suitable biocompatible material, such as polyethylene, ceramic and the like. The outer shell comprising the porous material 612 may be joined to the inner shell by any suitable method. In one example, a clip 616 may be located into a groove 618 defined in the outer shell. During installation, the inner shell may be located into the outer shell. Next, the clip 616 may be compressed and located inside the groove 618. Once the clip 616 is released, the clip 616 expands and nests in the groove 618 thereby capturing the inner shell.

Bores 622 may be defined through the cup 610 for accepting supplemental fasteners during implantation. In one example, the solid metal framework 614 is coated with hydroxyapatite to encourage bone ingrowth. In another example, biologics may be added to the porous material 612 such as demineralized bone matrix (DBM), bone morphogenetic proteins (BMP) and antibiotics. In addition, or alternatively, growth factors such as peptides or others may be added to the porous material.

Figure 20:
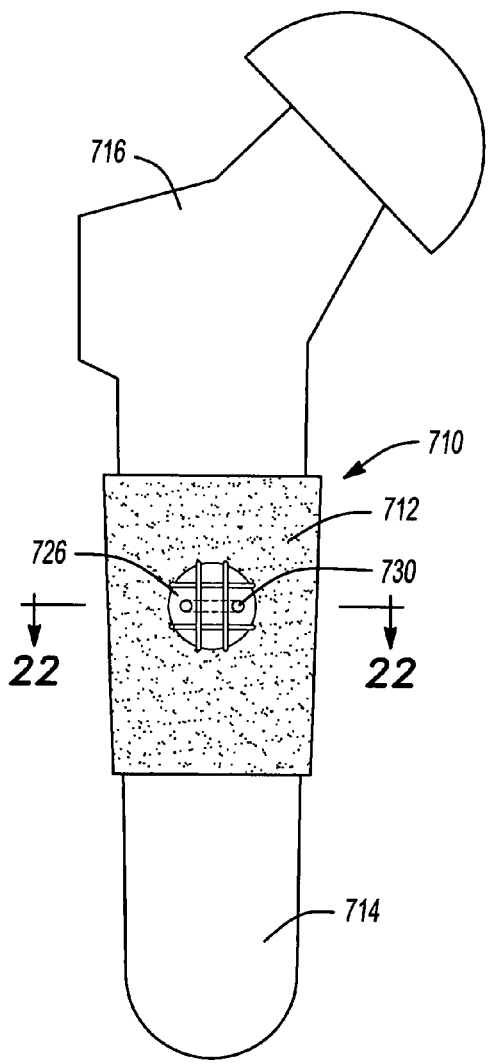
FIG. 20 is a side view of a porous insert shown in a secure position around a hip stem.
Figure 21:
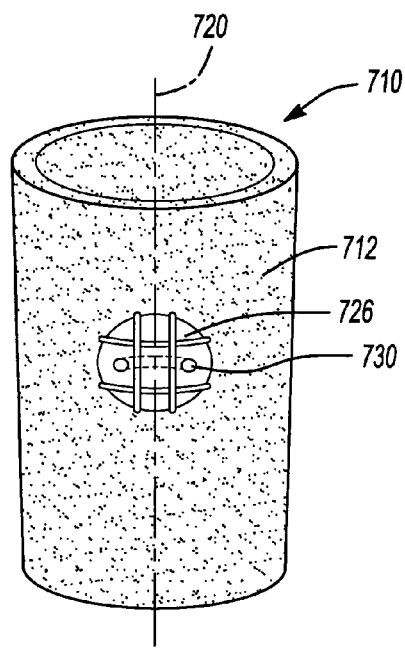
FIG. 21 is a perspective view of the porous insert of FIG. 20.
Figure 22:
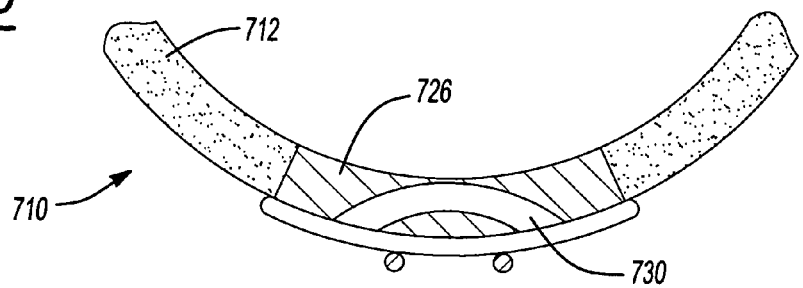
FIG. 22 is a sectional view of the porous insert taken along line 22-22 of FIG. 20.

With reference now to FIG. 20, an augment 710 in the form of a porous sheath or sleeve 712 is shown operatively secured to a stem 714 of a proximal humeral replacement 716. The sleeve 712 is formed of porous metal such as disclosed herein. In one example, the sleeve 712 may define a taper (FIG. 21) along its axis 720 for facilitating a press-fit around the sleeve 712 in an implanted position. The sleeve 712 may be slidably inserted around the distal stem until a press-fit or friction fit is attained, securing the augment 710 into a stable position. In an implanted position, the porous metal sleeve 712 provides biological fixation as bone grows up to and within the porous material. While the porous metal sleeve 712 is shown cooperatively engaged with a stem 714 of a proximal humeral replacement 716, it is appreciated that the sleeve 712 may be used in cooperation around other prosthesis incorporating stems such as a femoral hip replacement (see e.g., FIGS. 3A and 3B). Likewise, while the sleeve 712 is illustrated as tapered for providing a friction fit with the stem 714, it is appreciated that the sleeve 712 may be affixed to the stem 714 using other methods such as bone cement, fasteners and the like. While not specifically shown, the sleeve 712 may additionally incorporate attachment holes for soft and/or hard tissue ingrowth.

Providing a stand alone sleeve 712 allows pore size and thickness to be controlled during formation of the sleeve 712 without the concern of compromising the mechanical properties of the stem 714 as may be an issue when administering a porous coating onto the stem. In one example, pore size may be increased distally down the sleeve 712 to gradually reduce the stiffness of the stem 714 in an assembled position (FIG. 20). In addition, the stand alone sleeve 712 provides modularity whereby a series of sleeves may be provided having various dimensional properties. In one example, a solid metal area 726 may be defined on the sleeve 710 defining a passage 730. In this way, sutures or other attachment device may be inserted through the passage 730.

Figure 23:
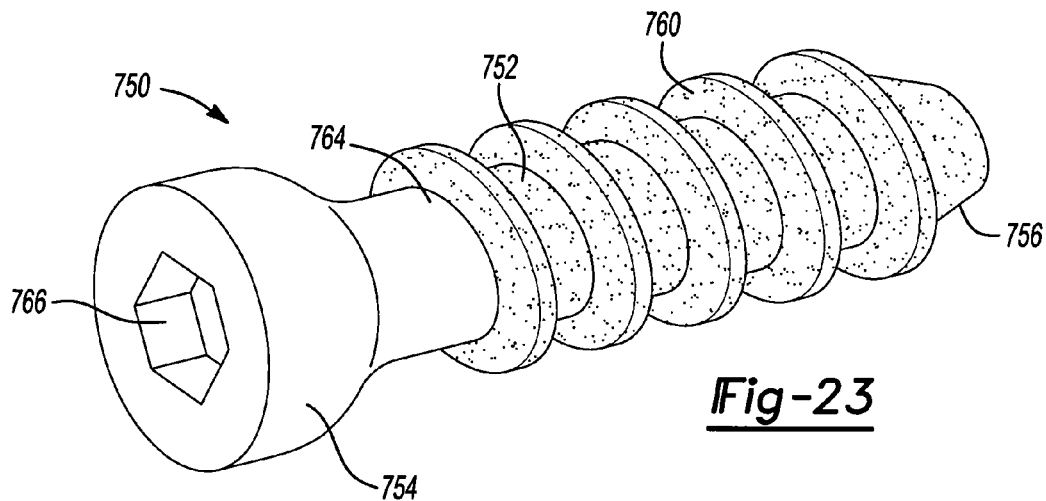
FIG. 23 is a perspective view of a prosthesis according to the present teachings.
Figure 24:
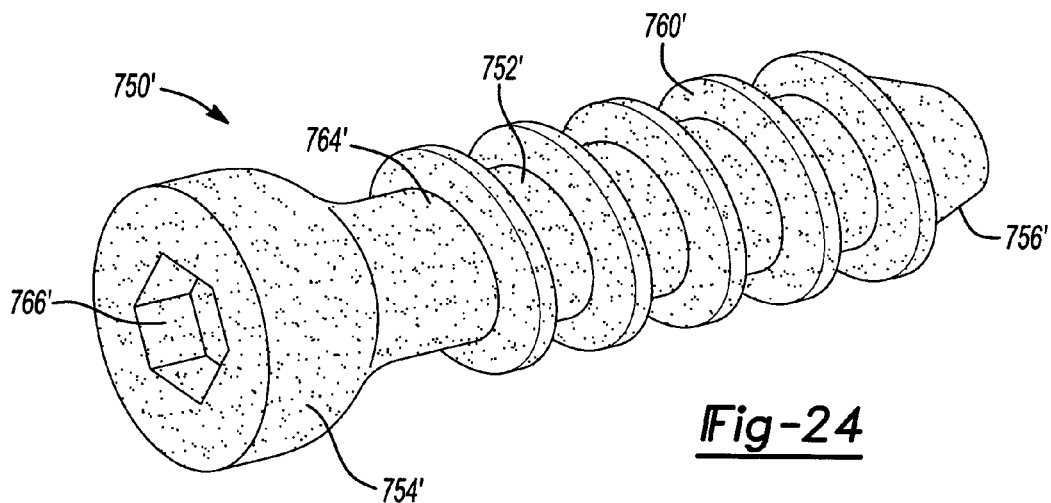
FIG. 24 is a perspective view of the prosthesis of FIG. 23 according to additional features.
Figure 25:
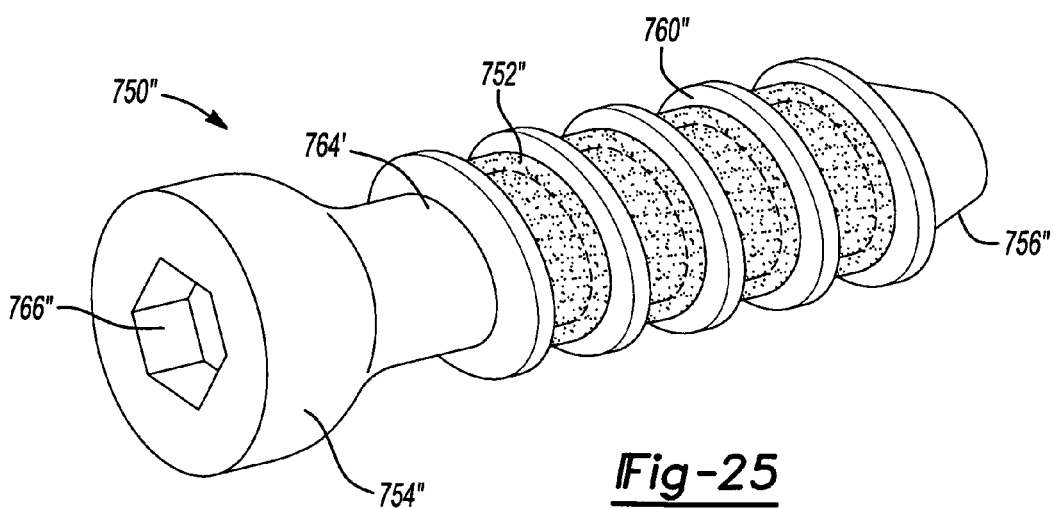
FIG. 25 is a perspective view of the prosthesis of FIG. 23 according to additional features.

Turning now to FIGS. 23-25, bone screws 750, 750' and 750" according to additional features is shown. With initial reference to FIG. 23, the bone screw 750 generally defines a longitudinal body 752 having a proximal end 754 and a distal end 756. Threads 760 are defined along the longitudinal body 752 between the distal end 756 and an intermediate portion 764 of the bone screw 750. Mating structure 766 is defined on the proximal end 754. The mating structure 766 defines a hex head adapted to receive a hex driver. Those skilled in the art will recognize that any mating structure may be provided at the proximal end suitable for engagement to a tool.

The bone screw 750, (FIG. 23) is formed of solid metal from the proximal end 754 to the intermediate portion 764 and porous metal from the intermediate portion 764 to the distal end 756. It is appreciated that the transition between solid metal and porous metal, identified at the intermediate portion 764 may be defined anywhere along the length of the longitudinal body 752. The solid metal and porous metal may comprise any suitable biocompatible metal such as stainless steel, titanium, titanium alloys, cobalt-chromium alloys and other materials. The bone screw 750' (FIG. 24) is formed entirely of porous metal. In one example, a series of bone screws having various porosities and dimensions may be provided. The bone screw 750" (FIG. 25) includes porous metal at the base of the threads 760" to a predetermined diameter.

According to additional features, anti-infective agents (i.e. antibiotics), osteoconductive agents (i.e. hydroxyapatite), autologous blood products activated by thrombin to induce clots (i.e. blood, platelet rich plasma, autologous stem cells derived from any location within the body), hydrogels, either alone or containing autologous or allogenic cells, peptides, or other biologically active ingredients that induce or aide bone formation (i.e. bone morphogenic proteins) may be added and/or infiltrated to the porous metal of the implants, augments, anchors and/or bone screws disclosed herein. Further, the porous metal structures described herein may also act as a carrier for bulk allograft or demineralized bone matrix products. Other growth promoters can be added and/or infiltered to the porous material of the implants, augments, anchors and bone screws described herein to promote appropriate soft or hard tissue response, ingrowth or attachment.

While the invention has been described in the specification and illustrated in the drawings with reference to various embodiments, it will be understood by those skilled in the art that various changes may be made and equivalents may be substituted for elements thereof without departing from the scope of the invention as defined in the claims. Furthermore, the mixing and matching of features, elements and/or functions between various embodiments is expressly contemplated herein so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the foregoing description and the appended claims.

What is claimed is:

1. A prosthesis comprising:
a stem defining an attachment surface; and
an insert collectively comprising a porous metal portion attached to a solid framework portion and having a fastener passage formed therethrough, said insert removably coupled to said stem, said insert adapted to be intraoperatively received at said attachment surface of said stem in a retained position, said solid framework portion including a series of frame portions arranged in a cross-hatched pattern that occupies a space on an outer surface of said insert and within an interior space of said insert, said solid framework portion operable to facilitate structural weight bearing properties of said porous insert; and
a fastener that passes through said fastener passage and threadably mates with said insert to couple said insert to said attachment surface of said stem;
wherein said insert is adapted to facilitate tissue ingrowth.

2. The prosthesis of claim 1 wherein said stem includes a femoral hip stem.

3. The prosthesis of claim 2 wherein said insert includes biocompatible metal.

4. The prosthesis of claim 2 wherein said insert is load bearing.

5. The prosthesis of claim 4, further comprising a plurality of inserts having distinct geometries, said plurality of inserts each adapted to be coupled to said attachment surface of said stem.

6. The prosthesis of claim 2 wherein said attachment surface is provided collectively on parallel surfaces of a proximal lateral surface of a calcar portion of said hip stem.

7. The prosthesis of claim 6 wherein said insert has a generally U-shaped body that wraps around said calcar portion of said hip stem and engages said parallel surfaces of said attachment surface.

8. The prosthesis of claim 7 wherein said attachment surface is nested in said calcar portion relative to an outer surface of said hip stem.

9. The prosthesis of claim 1 wherein said framework is coated with hydroxyapatite.

10. The prosthesis of claim 1 wherein said insert further includes at least one of an anti-infective agent, osteoconductive agent, autologous blood product, hydrogels, autologous cells, allogenic cells, peptides, bone morphogenetic proteins (BMP), bulk allograft and demineralized bone matrix (DBM).

11. The prosthesis of claim 1 wherein said solid framework portion is formed of metal.

12. The prosthesis of claim 11 wherein said solid framework portion is formed of a metal selected from the group comprising stainless steel, titanium, titanium alloys and cobalt-chromium alloys.

13. A prosthesis comprising:
a femoral hip stem having a calcar portion that has a recessed attachment surface that is formed around said calcar portion such that at least two surfaces of said recessed attachment surface occupy distinct planes and are substantially parallel, said hip stem including a threaded bore;
an insert comprising a porous metal portion and a distinct solid metal framework portion, said solid metal framework portion including a series of frame portions arranged in a cross-hatched pattern, said solid metal framework portion facilitating structural weight bearing properties of said insert, said insert having a generally U-shaped body that substantially wraps around said calcar portion and nests onto said recessed attachment surface in an installed position, said insert defining a throughbore; and
a fastener that extends through said throughbore and threadably mates with said threaded bore of said femoral hip stem in said installed position to intraoperatively couple said insert to said hip stem.

14. The prosthesis of claim 13 wherein said solid metal framework portion is formed exclusively on an outboard surface of said insert.

15. The prosthesis of claim 13 wherein said solid metal framework portion is formed of a metal selected from the group comprising stainless steel, titanium, titanium alloys and cobalt-chromium alloys.

16. The prosthesis of claim 13 wherein said solid metal framework portion is formed on an exterior surface of said insert and occupies an interior space of said insert.

* * * * *